US006521228B1

(12) United States Patent
Wiley et al.

(10) Patent No.: US 6,521,228 B1
(45) Date of Patent: Feb. 18, 2003

(54) ANTIBODIES DIRECTED AGAINST TRAIL

(75) Inventors: Steven R. Wiley, Seattle, WA (US); Raymond G. Goodwin, Seattle, WA (US)

(73) Assignee: Immunex Corporation, Seattle, WA (US)

(*) Notice: Subject to any disclaimer, the term of this patent is extended or adjusted under 35 U.S.C. 154(b) by 0 days.

(21) Appl. No.: 09/825,563

(22) Filed: Apr. 2, 2001

Related U.S. Application Data

(60) Division of application No. 09/320,424, filed on May 26, 1999, now Pat. No. 6,284,236, which is a continuation-in-part of application No. 09/190,046, filed on Nov. 10, 1998, now abandoned, which is a continuation-in-part of application No. 09/048,641, filed on Mar. 26, 1998, now abandoned, which is a continuation-in-part of application No. 08/670,354, filed on Jun. 25, 1996, now Pat. No. 5,763,223, which is a continuation-in-part of application No. 08/548,368, filed on Nov. 1, 1995, now abandoned, which is a continuation-in-part of application No. 08/496,632, filed on Jun. 29, 1995, now abandoned.

(51) Int. Cl.$^7$ ...................... A61K 39/395; C07K 16/24
(52) U.S. Cl. ................... 424/145.1; 435/325; 435/326; 530/387.1; 530/389.9; 530/388.1; 530/388.23; 530/388.24; 530/389.1; 530/389.2
(58) Field of Search ........................ 530/387.1, 389.9, 530/388.1, 388.23, 388.24, 389.1, 389.2; 424/130.1, 139.1, 145.1; 435/325, 326

(56) References Cited

U.S. PATENT DOCUMENTS

| 5,512,435 A | 4/1996 | Renschler et al. |
| 5,716,805 A | 2/1998 | Srinivasan et al. |
| 5,876,954 A | 3/1999 | Perron et al. |
| 6,030,945 A | 2/2000 | Ashkenazi |
| 6,046,048 A | 4/2000 | Ashkenazi et al. |

FOREIGN PATENT DOCUMENTS

| WO | WO 97/25428 | 7/1997 |
| WO | WO 97/33899 | 9/1997 |
| WO | WO 97/46686 | 12/1997 |
| WO | WO 99/07408 | 2/1999 |
| WO | WO 99/36535 | 7/1999 |
| WO | WO 99/48527 | 9/1999 |
| WO | WO 00/63253 | 10/2000 |

OTHER PUBLICATIONS

Banner et al., "Crystal structure of the soluble human 55 kd TNF receptor–human TNFβ complex: implications for TNF receptor activation," *Cell* 73: 431–445, 1993.

Bell, G.I. and Takeda, J., NCBI databank record, accession No. T10524, Jul. 28, 1993.

Belliveau et al., "Presence of the cytokine APO–2L (TRAIL), in the cerebrospinal fluid of multiple sclerosis patients," *Society for Neuroscience Abstracts* 23(1–2). 1997; p. 2207.

Belliveau et al., "Presence of the cytokine, APO–2L (TRAIL), in the cerebrospinal fluid of multiple sclerosis patients," Poster presented at the 27$^{th}$ Annual Meeting of the Society for Neuroscience, Oct. 25–30, 1997, New Orleans.

Beutler and van Huffel, "Unraveling function in the TNF ligand and receptor families," *Science* 264: 667–668, 1994.

Bowie, et al., "Deciphering the message in protein sequences: tolerance to amino acid substitutions," *Science* 247: 1306–1310, 1990.

Genexpress, NCBI databank record, accession No. Z36726, Aug. 18, 1994.

Goodwin et al., "Molecular cloning of a ligand for the inducible T cell gene 4–1BB: a member of an emerging family of cytokines with homology to tumor necrosis factor," *Eur. J. Immunol.* 23: 2631–2641, 1993.

Goodwin et al., "Study of the structure and function of Trail, a new member of the TNF ligand family," *Eur. Cytokine Network* 7(2): 166, 1996.

Gruss, H.–J. and Dower, S.K., "Tumor necrosis factor ligand superfamily: involvement in the pathology of malignant lymphomas," *Blood* 85(12): 3378–3404, 1995.

Hillier et al., NCBI databank record, accession No. T90422, Mar. 20, 1995.

Hillier et al., NCBI databank record, accession No. T82085, Mar. 10, 1995.

Hillier et al., NCBI databank record, accession No. R31020, Apr. 28, 1995.

Hollenbaugh et al., "Construction of immunoglobulin fusion proteins," *Current Protocols in Immunology, Supp.* 4, 1992, 10.19.1–10.19.11.

Hoppe et al., "A parallel three standard α–helical bundle at the nucleation site of collagen triple–helix formation," *FEBS Letters* 344: 191–195, 1994.

Jo, M. et al., "Apoptosis induced in normal human hepatocytes by tumor necrosis factor–related apoptosis–inducing ligand," *Nature Medicine* 6: 564–567, May 2000.

Kroemer, "The pharmacology of T cell apoptosis," *Adv. Immunol.* 58: 211–296, 1995.

Landschultz, et al., "The leucine zipper: a hypothetical structure common to a new class of DNA binding proteins," *Science* 240: 1759–1764, 1988.

Marsters et al., "Activation of apoptosis by Apo–2 ligand is independent of FADD but blocked by CrmA," *Current Biology* 6(6): 750, 1996.

Menard et al., "A gliotoxic factor and multiple sclerosis," *J Neurological Sciences* 154: 209–221, 1998.

(List continued on next page.)

*Primary Examiner*—Prema Mertz
(74) *Attorney, Agent, or Firm*—Kathryn A. Anderson

(57) ABSTRACT

A novel cytokine designated TRAIL induces apoptosis of certain target cells, including cancer cells and virally infected cells. Isolated DNA sequences encoding TRAIL are disclosed, along with expression vectors and transformed host cells useful in producing TRAIL polypeptides. Antibodies that specifically bind TRAIL are provided as well.

35 Claims, 4 Drawing Sheets

OTHER PUBLICATIONS

Mikayama, T. et al., "Molecular cloning and functional expression of a cDNA encoding glycosylation–inhibiting factor," *Proc. Natl. Acad. Sci. USA 90*:10056–10060, 1993.

O'Mahoney et al., "An immune suppressive factor derived from esophageal squamous carcinoma induces apoptosis in normal and transformed cells of lymphoid lineage," *J. Immunol. 151(9)*: 4847–4856, 1993.

Pitti et al., "Induction of apoptosis by Apo–2 ligand, a new member of the tumor necrosis factor cytokine family," *J. Biol. Chem. 271(22)*: 12687–12690, 1996.

Reiger, F. and J. Belliveau, report on research studies, in letter dated Aug. 31, 1999.

Rieger, R. et al., Glossary of Genetics and Cytogenetics, Fourth Ed., Springer–Verlag, pp. 16–19, 1976.

Sachs and Lotem, "Control of programmed cell death in normal and leukemic cells: new implications for therapy," *Blood 82(1)*: 15–21, 1993.

Smith et al., "The TNF receptor superfamily of cellular and viral proteins: activation, costimulation, and death," *Cell 76*: 959–962, 1994.

Smith et al., "CD30 Antigen, a marker for Hodgkin's Lymphoma, is a receptor whose ligand defines an emerging family of cytokines with homology to TNF," *Cell 73*: 1349–1360, 1993.

Smith et al., "Trail: a new member of the TNF ligand family that induces apoptosis," *Eur. Cytokine Network 7(3)*: 429, 1996.

Suda et al., "Molecular cloning and expression of the Fas ligand, a novel member of the tumor necrosis factor family," *Cell 75*: 1169–1178, 1993.

Takahashi et al., "Human Fas ligand: gene structure, chromosomal location and species specificity," *International Immunol. 6(10)*: 1567–1574, 1994.

Takeda et al., "A molecular inventory of human pancreatic islets: sequence analysis of 1000 cDNA clones," *Human Molecular Genetics 2(11)*: 1793–1798, 1993.

Voet et al., Biochemistry, John Wiley & Sons, Inc., pp. 126–128 and 228–234, 1990.

Wiley et al., "Identification and characterization of a new member of the TNF family that induces apoptosis," *Immunity 3*:673–682, 1995.

Wong et al., "Antiviral properties of TNF," in *Tumor Necrosis Factors: The Molecules and Their Emerging Role in Medicine*, Raven Press, Ltd., New York, 1992, 371–381.

FIGURE 3

```
ATGGCTACAGGCTCCCGGACGTCCCTGCTCCTGGCTTTTGGCCTGCTCTGCCTGCCCTGG
 M  A  T  G  S  R  T  S  L  L  L  A  F  G  L  L  C  L  P  W

CTTCAAGAGGGCAGTGCAACTAGTTCTGACCGTATGAAACAGATAGAGGATAAGATCGAA
 L  Q  E  G  S  A  T  S  S  D  R  M  K  Q  I  E  D  K  I  E

GAGATCCTAAGTAAGATTTATCATATAGAGAATGAAATCGCCCGTATCAAAAAGCTGATT
 E  I  L  S  K  I  Y  H  I  E  N  E  I  A  R  I  K  K  L  I

GGCGAGCGGACTAGATCTACCTCTGAGGAAACCATTTCTACAGTTCAAGAAAAGCAACAA
 G  E  R  T  R  S  T  S  E  E  T  I  S  T  V  Q  E  K  Q  Q

AATATTTCTCCCCTAGTGAGAGAAAGAGGTCCTCAGAGAGTAGCAGCTCACATAACTGGG
 N  I  S  P  L  V  R  E  R  G  P  Q  R  V  A  A  H  I  T  G

ACCAGAGGAAGAAGCAACACATTGTCTTCTCCAAACTCCAAGAATGAAAAGGCTCTGGGC
 T  R  G  R  S  N  T  L  S  S  P  N  S  K  N  E  K  A  L  G

CGCAAAATAAACTCCTGGGAATCATCAAGGAGTGGGCATTCATTCCTGAGCAACTTGCAC
 R  K  I  N  S  W  E  S  S  R  S  G  H  S  F  L  S  N  L  H

TTGAGGAATGGTGAACTGGTCATCCATGAAAAGGGTTTTACTACATCTATTCCCAAACA
 L  R  N  G  E  L  V  I  H  E  K  G  F  Y  Y  I  Y  S  Q  T

TACTTTCGATTTCAGGAGGAAATAAAAGAAAACACAAAGAACGACAAACAAATGGTCCAA
 Y  F  R  F  Q  E  E  I  K  E  N  T  K  N  D  K  Q  M  V  Q

TATATTTACAAATACACAAGTTATCCTGACCCTATATTGTTGATGAAAAGTGCTAGAAAT
 Y  I  Y  K  Y  T  S  Y  P  D  P  I  L  L  M  K  S  A  R  N

AGTTGTTGGTCTAAAGATGCAGAATATGGACTCTATTCCATCTATCAAGGGGGAATATTT
 S  C  W  S  K  D  A  E  Y  G  L  Y  S  I  Y  Q  G  G  I  F

GAGCTTAAGGAAAATGACAGAATTTTTGTTTCTGTAACAAATGAGCACTTGATAGACATG
 E  L  K  E  N  D  R  I  F  V  S  V  T  N  E  H  L  I  D  M

GACCATGAAGCCAGTTTTTTCGGGGCCTTTTTAGTTGGC
 D  H  E  A  S  F  F  G  A  F  L  V  G
```

FIGURE 4

```
ATGGCTCGGAGGCTATGGATCTTGAGCTTATTAGCCGTGACCTTGACGGTGGCTTTGGCG
 M   A   R   R   L   W   I   L   S   L   L   A   V   T   L   T   V   A   L   A

GCACCTTCTCAGAAATCGAAGCGCAGGACTAGTTCTGACCGTATGAAACAGATAGAGGAT
 A   P   S   Q   K   S   K   R   R   T   S   S   D   R   M   K   Q   I   E   D

AAGATCGAAGAGATCCTAAGTAAGATTTATCATATAGAGAATGAAATCGCCCGTATCAAA
 K   I   E   E   I   L   S   K   I   Y   H   I   E   N   E   I   A   R   I   K

AAGCTGATTGGCGAGCGGACTAGATCTACCTCTGAGGAAACCATTTCTACAGTTCAAGAA
 K   L   I   G   E   R   T   R   S   T   S   E   E   T   I   S   T   V   Q   E

AAGCAACAAAATATTTCTCCCCTAGTGAGAGAAAGAGGTCCTCAGAGAGTAGCAGCTCAC
 K   Q   Q   N   I   S   P   L   V   R   E   R   G   P   Q   R   V   A   A   H

ATAACTGGGACCAGAGGAAGAAGCAACACATTGTCTTCTCCAAACTCCAAGAATGAAAAG
 I   T   G   T   R   G   R   S   N   T   L   S   S   P   N   S   K   N   E   K

GCTCTGGGCCGCAAAATAAACTCCTGGGAATCATCAAGGAGTGGGCATTCATTCCTGAGC
 A   L   G   R   K   I   N   S   W   E   S   S   R   S   G   H   S   F   L   S

AACTTGCACTTGAGGAATGGTGAACTGGTCATCCATGAAAAAGGGTTTTACTACATCTAT
 N   L   H   L   R   N   G   E   L   V   I   H   E   K   G   F   Y   Y   I   Y

TCCCAAACATACTTTCGATTTCAGGAGGAAATAAAAGAAAACACAAAGAACGACAAACAA
 S   Q   T   Y   F   R   F   Q   E   E   I   K   E   N   T   K   N   D   K   Q

ATGGTCCAATATATTTACAAATACACAAGTTATCCTGACCCTATATTGTTGATGAAAAGT
 M   V   Q   Y   I   Y   K   Y   T   S   Y   P   D   P   I   L   L   M   K   S

GCTAGAAATAGTTGTTGGTCTAAAGATGCAGAATATGGACTCTATTCCATCTATCAAGGG
 A   R   N   S   C   W   S   K   D   A   E   Y   G   L   Y   S   I   Y   Q   G

GGAATATTTGAGCTTAAGGAAAATGACAGAATTTTTGTTTCTGTAACAAATGAGCACTTG
 G   I   F   E   L   K   E   N   D   R   I   F   V   S   V   T   N   E   H   L

ATAGACATGGACCATGAAGCCAGTTTTTTCGGGGCCTTTTTAGTTGGC
 I   D   M   D   H   E   A   S   F   F   G   A   F   L   V   G
```

SEQUENCE LISTING

<160> NUMBER OF SEQ ID NOS: 25

<210> SEQ ID NO 1
<211> LENGTH: 1751
<212> TYPE: DNA
<213> ORGANISM: human
<220> FEATURE:
<221> NAME/KEY: CDS
<222> LOCATION: (88)..(933)

-continued

<400> SEQUENCE: 1

```
cctcactgac tataaagaa tagagaagga agggcttcag tgaccggctg cctggctgac        60
ttacagcagt cagactctga caggatc atg gct atg atg gag gtc cag ggg gga     114
                               Met Ala Met Met Glu Val Gln Gly Gly
                                 1               5 ccc agc ctg gga cag acc tgc gtg ctg atc gtg atc ttc aca gtg ctc       162
Pro Ser Leu Gly Gln Thr Cys Val Leu Ile Val Ile Phe Thr Val Leu
 10              15                  20                  25 ctg cag tct ctc tgt gtg gct gta act tac gtg tac ttt acc aac gag       210
Leu Gln Ser Leu Cys Val Ala Val Thr Tyr Val Tyr Phe Thr Asn Glu
                 30                  35                  40 ctg aag cag atg cag gac aag tac tcc aaa agt ggc att gct tgt ttc       258
Leu Lys Gln Met Gln Asp Lys Tyr Ser Lys Ser Gly Ile Ala Cys Phe
             45                  50                  55 tta aaa gaa gat gac agt tat tgg gac ccc aat gac gaa gag agt atg       306
Leu Lys Glu Asp Asp Ser Tyr Trp Asp Pro Asn Asp Glu Glu Ser Met
         60                  65                  70 aac agc ccc tgc tgg caa gtc aag tgg caa ctc cgt cag ctc gtt aga       354
Asn Ser Pro Cys Trp Gln Val Lys Trp Gln Leu Arg Gln Leu Val Arg
     75                  80                  85 aag atg att ttg aga acc tct gag gaa acc att tct aca gtt caa gaa       402
Lys Met Ile Leu Arg Thr Ser Glu Glu Thr Ile Ser Thr Val Gln Glu
 90                  95                 100                 105 aag caa caa aat att tct ccc cta gtg aga gaa aga ggt cct cag aga       450
Lys Gln Gln Asn Ile Ser Pro Leu Val Arg Glu Arg Gly Pro Gln Arg
                110                 115                 120 gta gca gct cac ata act ggg acc aga gga aga agc aac aca ttg tct       498
Val Ala Ala His Ile Thr Gly Thr Arg Gly Arg Ser Asn Thr Leu Ser
            125                 130                 135 tct cca aac tcc aag aat gaa aag gct ctg ggc cgc aaa ata aac tcc       546
Ser Pro Asn Ser Lys Asn Glu Lys Ala Leu Gly Arg Lys Ile Asn Ser
        140                 145                 150 tgg gaa tca tca agg agt ggg cat tca ttc ctg agc aac ttg cac ttg       594
Trp Glu Ser Ser Arg Ser Gly His Ser Phe Leu Ser Asn Leu His Leu
    155                 160                 165 agg aat ggt gaa ctg gtc atc cat gaa aaa ggg ttt tac tac atc tat       642
Arg Asn Gly Glu Leu Val Ile His Glu Lys Gly Phe Tyr Tyr Ile Tyr
170                 175                 180                 185 tcc caa aca tac ttt cga ttt cag gag gaa ata aaa gaa aac aca aag       690
Ser Gln Thr Tyr Phe Arg Phe Gln Glu Glu Ile Lys Glu Asn Thr Lys
                190                 195                 200 aac gac aaa caa atg gtc caa tat att tac aaa tac aca agt tat cct       738
Asn Asp Lys Gln Met Val Gln Tyr Ile Tyr Lys Tyr Thr Ser Tyr Pro
            205                 210                 215 gac cct ata ttg ttg atg aaa agt gct aga aat agt tgt tgg tct aaa       786
Asp Pro Ile Leu Leu Met Lys Ser Ala Arg Asn Ser Cys Trp Ser Lys
        220                 225                 230 gat gca gaa tat gga ctc tat tcc atc tat caa ggg gga ata ttt gag       834
Asp Ala Glu Tyr Gly Leu Tyr Ser Ile Tyr Gln Gly Gly Ile Phe Glu
    235                 240                 245 ctt aag gaa aat gac aga att ttt gtt tct gta aca aat gag cac ttg       882
Leu Lys Glu Asn Asp Arg Ile Phe Val Ser Val Thr Asn Glu His Leu
250                 255                 260                 265 ata gac atg gac cat gaa gcc agt ttt ttc ggg gcc ttt tta gtt ggc       930
Ile Asp Met Asp His Glu Ala Ser Phe Phe Gly Ala Phe Leu Val Gly
                270                 275                 280 taa ctgacctgga agaaaaagc aataacctca aagtgactat tcagttttca            983
```

-continued

```
ggatgataca ctatgaagat gtttcaaaaa atctgaccaa acaaacaaa cagaaaacag    1043 aaaacaaaaa aacctctatg caatctgagt agagcagcca caaccaaaaa attctacaac   1103
acacactgtt ctgaaagtga ctcacttatc ccaagaaaat gaaattgctg aaagatcttt   1163
caggactcta cctcatatca gtttgctagc agaaatctag aagactgtca gcttccaaac   1223
attaatgcaa tggttaacat cttctgtctt tataatctac tccttgtaaa gactgtagaa   1283
gaaagcgcaa caatccatct ctcaagtagt gtatcacagt agtagcctcc aggtttcctt   1343
aagggacaac atccttaagt caaagagag aagaggcacc actaaaagat cgcagtttgc    1403
ctggtgcagt ggctcacacc tgtaatccca acattttggg aacccaaggt gggtagatca   1463
cgagatcaag agatcaagac catagtgacc aacatagtga aacccatct ctactgaaag    1523 tgcaaaaatt agctgggtgt gttggcacat gcctgtagtc ccagctactt gagaggctga   1583
ggcaggagaa tcgtttgaac ccgggaggca gaggttgcag tgtggtgaga tcatgccact   1643
acactccagc ctggcgacag agcgagactt ggtttcaaaa aaaaaaaaa aaaaaaactt    1703 cagtaagtac gtgttatttt tttcaataaa attctattac agtatgtc               1751
```

<210> SEQ ID NO 2
<211> LENGTH: 281
<212> TYPE: PRT
<213> ORGANISM: human

<400> SEQUENCE: 2

```
Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240
```

```
Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 3
<211> LENGTH: 1521
<212> TYPE: DNA
<213> ORGANISM: human
<220> FEATURE:
<221> NAME/KEY: CDS
<222> LOCATION: (78)..(383)

<400> SEQUENCE: 3
aattccggaa tagagaagga agggcttcag tgaccggctg cctggctgac ttacagcagt    60
cagactctga caggatc atg gct atg atg gag gtc cag ggg gga ccc agc     110
                  Met Ala Met Met Glu Val Gln Gly Gly Pro Ser
                   1               5                  10 ctg gga cag acc tgc gtg ctg atc gtg atc ttc aca gtg ctc ctg cag    158
Leu Gly Gln Thr Cys Val Leu Ile Val Ile Phe Thr Val Leu Leu Gln
             15                  20                  25 tct ctc tgt gtg gct gta act tac gtg tac ttt acc aac gag ctg aag    206
Ser Leu Cys Val Ala Val Thr Tyr Val Tyr Phe Thr Asn Glu Leu Lys
         30                  35                  40 cag atg cag gac aag tac tcc aaa agt ggc att gct tgt ttc tta aaa    254
Gln Met Gln Asp Lys Tyr Ser Lys Ser Gly Ile Ala Cys Phe Leu Lys
     45                  50                  55 gaa gat gac agt tat tgg gac ccc aat gac gaa gag agt atg aac agc    302
Glu Asp Asp Ser Tyr Trp Asp Pro Asn Asp Glu Glu Ser Met Asn Ser
 60                  65                  70                  75 ccc tgc tgg caa gtc aag tgg caa ctc cgt cag ctc gtt aga aag act    350
Pro Cys Trp Gln Val Lys Trp Gln Leu Arg Gln Leu Val Arg Lys Thr
                 80                  85                  90 cca aga atg aaa agg ctc tgg gcc gca aaa taa actcctggga atcatcaagg   403
Pro Arg Met Lys Arg Leu Trp Ala Ala Lys
             95                 100 agtgggcatt cattcctgag caacttgcac ttgaggaatg gtgaactggt catccatgaa   463
aaagggtttt actacatcta ttcccaaaca tactttcgat ttcaggagga aataaaagaa   523
aacacaaaga acgacaaaca aatggtccaa tatatttaca aatacacaag ttatcctgac   583
cctatattgt tgatgaaaag tgctagaaat agttgttggt ctaaagatgc agaatatgga   643
ctctattcca tctatcaagg gggaatattt gagcttaagg aaaatgacag aattttttgtt   703 tctgtaacaa atgagcactt gatagacatg gaccatgaag ccagtttttt cggggccttt   763
ttagttggct aactgacctg gaagaaaaaa gcaataaccct caaagtgact attcagtttt   823
caggatgata cactatgaag atgtttcaaa aaatctgacc aaaacaaaca aacagaaaac   883
agaaaacaaa aaaccctcta tgcaatctga gtagagcagc cacaaccaaa aaattctaca   943
acacacactg ttctgaaagt gactcactta tcccaagaga atgaaattgc tgaaagatct  1003
ttcaggactc tacctcatat cagtttgcta gcagaaatct agaagactgt cagcttccaa  1063
acattaatgc agtggttaac atcttctgtc tttataatct actccttgta aagactgtag  1123
aagaaagcgc aacaatccat ctctcaagta gtgtatcaca gtagtagcct ccaggttttcc  1183 ttaagggaca catccttaa gtcaaaagag agaagaggca ccactaaaag atcgcagttt   1243
gcctggtgca gtggctcaca cctgtaatcc caacattttg ggaacccaag gtgggtagat  1303
```

```
cacgagatca agagatcaag accatagtga ccaacatagt gaaacccccat ctctactgaa      1363 agtgcaaaaa ttagctgggt gtgttggcac atgcctgtag tcccagctac ttgagaggct      1423
gaggcaggag aatcgtttga acccgggagg cagaggttgc agtgtggtga gatcatgcca      1483
ctacactcca gcctggcgac agagcgagac ttggtttc                              1521
```

<210> SEQ ID NO 4
<211> LENGTH: 101
<212> TYPE: PRT
<213> ORGANISM: human

<400> SEQUENCE: 4

```
Met Ala Met Met Glu Val Gln Gly Gly Pro Ser Leu Gly Gln Thr Cys
 1               5                  10                  15
Val Leu Ile Val Ile Phe Thr Val Leu Leu Gln Ser Leu Cys Val Ala
            20                  25                  30
Val Thr Tyr Val Tyr Phe Thr Asn Glu Leu Lys Gln Met Gln Asp Lys
        35                  40                  45
Tyr Ser Lys Ser Gly Ile Ala Cys Phe Leu Lys Glu Asp Asp Ser Tyr
    50                  55                  60
Trp Asp Pro Asn Asp Glu Glu Ser Met Asn Ser Pro Cys Trp Gln Val
65                  70                  75                  80
Lys Trp Gln Leu Arg Gln Leu Val Arg Lys Thr Pro Arg Met Lys Arg
                85                  90                  95
Leu Trp Ala Ala Lys
            100
```

<210> SEQ ID NO 5
<211> LENGTH: 1366
<212> TYPE: DNA
<213> ORGANISM: murine
<220> FEATURE:
<221> NAME/KEY: CDS
<222> LOCATION: (47)..(919)

<400> SEQUENCE: 5

```
tgctgggctg caagtctgca ttgggaagtc agacctggac agcagt atg cct tcc          55
                                               Met Pro Ser
                                                 1 tca ggg gcc ctg aag gac ctc agc ttc agt cag cac ttc agg atg atg       103
Ser Gly Ala Leu Lys Asp Leu Ser Phe Ser Gln His Phe Arg Met Met
        5                   10                  15 gtg att tgc ata gtg ctc ctg cag gtg ctc ctg cag gct gtg tct gtg       151
Val Ile Cys Ile Val Leu Leu Gln Val Leu Leu Gln Ala Val Ser Val
 20                  25                  30                  35 gct gtg act tac atg tac ttc acc aac gag atg aag cag ctg cag gac       199
Ala Val Thr Tyr Met Tyr Phe Thr Asn Glu Met Lys Gln Leu Gln Asp
                40                  45                  50 aat tac tcc aaa att gga cta gct tgc ttc tca aag acg gat gag gat       247
Asn Tyr Ser Lys Ile Gly Leu Ala Cys Phe Ser Lys Thr Asp Glu Asp
            55                  60                  65 ttc tgg gac tcc act gat gga gag atc ttg aac aga ccc tgc ttg cag       295
Phe Trp Asp Ser Thr Asp Gly Glu Ile Leu Asn Arg Pro Cys Leu Gln
        70                  75                  80 gtt aag agg caa ctg tat cag ctc att gaa gag gtg act ttg aga acc       343
Val Lys Arg Gln Leu Tyr Gln Leu Ile Glu Glu Val Thr Leu Arg Thr
    85                  90                  95 ttt cag gac acc att tct aca gtt cca gaa aag cag cta agt act cct       391
Phe Gln Asp Thr Ile Ser Thr Val Pro Glu Lys Gln Leu Ser Thr Pro
```

```
                                                                              -continued
100               105               110               115
ccc ttg ccc aga ggt gga aga cct cag aaa gtg gca gct cac att act    439
Pro Leu Pro Arg Gly Gly Arg Pro Gln Lys Val Ala Ala His Ile Thr
                120               125               130 ggg atc act cgg aga agc aac tca gct tta att cca atc tcc aag gat    487
Gly Ile Thr Arg Arg Ser Asn Ser Ala Leu Ile Pro Ile Ser Lys Asp
        135               140               145 gga aag acc tta ggc cag aag att gaa tcc tgg gag tcc tct cgg aaa    535
Gly Lys Thr Leu Gly Gln Lys Ile Glu Ser Trp Glu Ser Ser Arg Lys
    150               155               160 ggg cat tca ttt ctc aac cac gtg ctc ttt agg aat gga gag ctg gtc    583
Gly His Ser Phe Leu Asn His Val Leu Phe Arg Asn Gly Glu Leu Val
165               170               175 atc gag cag gag ggc ctg tat tac atc tat tcc caa aca tac ttc cga    631
Ile Glu Gln Glu Gly Leu Tyr Tyr Ile Tyr Ser Gln Thr Tyr Phe Arg
180               185               190               195 ttt cag gaa gct gaa gac gct tcc aag atg gtc tca aag gac aag gtg    679
Phe Gln Glu Ala Glu Asp Ala Ser Lys Met Val Ser Lys Asp Lys Val
                200               205               210 aga acc aaa cag ctg gtg cag tac atc tac aag tac acc agc tat ccg    727
Arg Thr Lys Gln Leu Val Gln Tyr Ile Tyr Lys Tyr Thr Ser Tyr Pro
            215               220               225 gat ccc ata gtg ctc atg aag agc gcc aga aac agc tgt tgg tcc aga    775
Asp Pro Ile Val Leu Met Lys Ser Ala Arg Asn Ser Cys Trp Ser Arg
        230               235               240 gat gcc gag tac gga ctg tac tcc atc tat cag gga gga ttg ttc gag    823
Asp Ala Glu Tyr Gly Leu Tyr Ser Ile Tyr Gln Gly Gly Leu Phe Glu
    245               250               255 cta aaa aaa aat gac agg att ttt gtt tct gtg aca aat gaa cat ttg    871
Leu Lys Lys Asn Asp Arg Ile Phe Val Ser Val Thr Asn Glu His Leu
260               265               270               275 atg gac ctg gat caa gaa gcc agc ttc ttt gga gcc ttt tta att aac    919
Met Asp Leu Asp Gln Glu Ala Ser Phe Phe Gly Ala Phe Leu Ile Asn
                280               285               290 taaatgacca gtaaagatca aacacagccc taaagtaccc agtaatcttc taggttgaag    979
gcatgcctgg aaagcgactg aactggttag gatatggcct ggctgtagaa acctcaggac   1039
agatgtgaca gaaaggcagc tggaactcag cagcgacagg ccaacagtcc agccacagac   1099
actttcggtg tttcatcgag agacttgctt tctttccgca aaatgagatc actgtagcct   1159
ttcaatgatc tacctggtat cagtttgcag agatctagaa gacgtccagt ttctaaatat   1219
ttatgcaaca attgacaatt ttcaccttg ttatctggtc caggggtgta aagccaagtg    1279
ctcacaagct gtgtgcagac caggatagct atgaatgcag gtcagcataa aaatcacaga   1339
atatctcacc tactaaaaaa aaaaaaa                                       1366

<210> SEQ ID NO 6
<211> LENGTH: 291
<212> TYPE: PRT
<213> ORGANISM: murine

<400> SEQUENCE: 6

Met Pro Ser Ser Gly Ala Leu Lys Asp Leu Ser Phe Ser Gln His Phe
1               5                   10                  15

Arg Met Met Val Ile Cys Ile Val Leu Leu Gln Val Leu Leu Gln Ala
                20                  25                  30

Val Ser Val Ala Val Thr Tyr Met Tyr Phe Thr Asn Glu Met Lys Gln
            35                  40                  45
```

```
Leu Gln Asp Asn Tyr Ser Lys Ile Gly Leu Ala Cys Phe Ser Lys Thr
        50                  55                  60

Asp Glu Asp Phe Trp Asp Ser Thr Asp Gly Glu Ile Leu Asn Arg Pro
 65                  70                  75                  80

Cys Leu Gln Val Lys Arg Gln Leu Tyr Gln Leu Ile Glu Glu Val Thr
                 85                  90                  95

Leu Arg Thr Phe Gln Asp Thr Ile Ser Thr Val Pro Glu Lys Gln Leu
                100                 105                 110

Ser Thr Pro Pro Leu Pro Arg Gly Gly Arg Pro Gln Lys Val Ala Ala
                115                 120                 125

His Ile Thr Gly Ile Thr Arg Arg Ser Asn Ser Ala Leu Ile Pro Ile
        130                 135                 140

Ser Lys Asp Gly Lys Thr Leu Gly Gln Lys Ile Glu Ser Trp Glu Ser
145                 150                 155                 160

Ser Arg Lys Gly His Ser Phe Leu Asn His Val Leu Phe Arg Asn Gly
                165                 170                 175

Glu Leu Val Ile Glu Gln Glu Gly Leu Tyr Tyr Ile Tyr Ser Gln Thr
                180                 185                 190

Tyr Phe Arg Phe Gln Glu Ala Glu Asp Ala Ser Lys Met Val Ser Lys
                195                 200                 205

Asp Lys Val Arg Thr Lys Gln Leu Val Gln Tyr Ile Tyr Lys Tyr Thr
        210                 215                 220

Ser Tyr Pro Asp Pro Ile Val Leu Met Lys Ser Ala Arg Asn Ser Cys
225                 230                 235                 240

Trp Ser Arg Asp Ala Glu Tyr Gly Leu Tyr Ser Ile Tyr Gln Gly Gly
                245                 250                 255

Leu Phe Glu Leu Lys Lys Asn Asp Arg Ile Phe Val Ser Val Thr Asn
                260                 265                 270

Glu His Leu Met Asp Leu Asp Gln Glu Ala Ser Phe Phe Gly Ala Phe
        275                 280                 285

Leu Ile Asn
        290

<210> SEQ ID NO 7
<211> LENGTH: 8
<212> TYPE: PRT
<213> ORGANISM: synthetic

<400> SEQUENCE: 7

Asp Tyr Lys Asp Asp Asp Asp Lys
 1               5

<210> SEQ ID NO 8
<211> LENGTH: 17
<212> TYPE: PRT
<213> ORGANISM: conserved peptide
<220> FEATURE:

<400> SEQUENCE: 8

Leu Val Val Xaa Xaa Xaa Gly Leu Tyr Tyr Val Tyr Xaa Gln Val Xaa
 1               5                  10                  15

Phe

<210> SEQ ID NO 9
<211> LENGTH: 32
<212> TYPE: PRT
<213> ORGANISM: CMV leader
```

-continued

```
<400> SEQUENCE: 9

Met Ala Arg Arg Leu Trp Ile Leu Ser Leu Leu Ala Val Thr Leu Thr
 1               5                  10                  15

Val Ala Leu Ala Ala Pro Ser Gln Lys Ser Lys Arg Arg Thr Ser Ser
             20                  25                  30

<210> SEQ ID NO 10
<211> LENGTH: 759
<212> TYPE: DNA
<213> ORGANISM: synthetic fusion
<220> FEATURE:
<221> NAME/KEY: CDS
<222> LOCATION: (1)..(759)

<400> SEQUENCE: 10 atg gct aca ggc tcc cgg acg tcc ctg ctc ctg gct ttt ggc ctg ctc      48
Met Ala Thr Gly Ser Arg Thr Ser Leu Leu Leu Ala Phe Gly Leu Leu
 1               5                  10                  15 tgc ctg ccc tgg ctt caa gag ggc agt gca act agt tct gac cgt atg      96
Cys Leu Pro Trp Leu Gln Glu Gly Ser Ala Thr Ser Ser Asp Arg Met
             20                  25                  30 aaa cag ata gag gat aag atc gaa gag atc cta agt aag att tat cat     144
Lys Gln Ile Glu Asp Lys Ile Glu Glu Ile Leu Ser Lys Ile Tyr His
         35                  40                  45 ata gag aat gaa atc gcc cgt atc aaa aag ctg att ggc gag cgg act     192
Ile Glu Asn Glu Ile Ala Arg Ile Lys Lys Leu Ile Gly Glu Arg Thr
     50                  55                  60 aga tct acc tct gag gaa acc att tct aca gtt caa gaa aag caa caa     240
Arg Ser Thr Ser Glu Glu Thr Ile Ser Thr Val Gln Glu Lys Gln Gln
 65                  70                  75                  80 aat att tct ccc cta gtg aga gaa aga ggt cct cag aga gta gca gct     288
Asn Ile Ser Pro Leu Val Arg Glu Arg Gly Pro Gln Arg Val Ala Ala
                 85                  90                  95 cac ata act ggg acc aga gga aga agc aac aca ttg tct tct cca aac     336
His Ile Thr Gly Thr Arg Gly Arg Ser Asn Thr Leu Ser Ser Pro Asn
            100                 105                 110 tcc aag aat gaa aag gct ctg ggc cgc aaa ata aac tcc tgg gaa tca     384
Ser Lys Asn Glu Lys Ala Leu Gly Arg Lys Ile Asn Ser Trp Glu Ser
        115                 120                 125 tca agg agt ggg cat tca ttc ctg agc aac ttg cac ttg agg aat ggt     432
Ser Arg Ser Gly His Ser Phe Leu Ser Asn Leu His Leu Arg Asn Gly
    130                 135                 140 gaa ctg gtc atc cat gaa aaa ggg ttt tac tac atc tat tcc caa aca     480
Glu Leu Val Ile His Glu Lys Gly Phe Tyr Tyr Ile Tyr Ser Gln Thr
145                 150                 155                 160 tac ttt cga ttt cag gag gaa ata aaa gaa aac aca aag aac gac aaa     528
Tyr Phe Arg Phe Gln Glu Glu Ile Lys Glu Asn Thr Lys Asn Asp Lys
                165                 170                 175 caa atg gtc caa tat att tac aaa tac aca agt tat cct gac cct ata     576
Gln Met Val Gln Tyr Ile Tyr Lys Tyr Thr Ser Tyr Pro Asp Pro Ile
            180                 185                 190 ttg ttg atg aaa agt gct aga aat agt tgt tgg tct aaa gat gca gaa     624
Leu Leu Met Lys Ser Ala Arg Asn Ser Cys Trp Ser Lys Asp Ala Glu
        195                 200                 205 tat gga ctc tat tcc atc tat caa ggg gga ata ttt gag ctt aag gaa     672
Tyr Gly Leu Tyr Ser Ile Tyr Gln Gly Gly Ile Phe Glu Leu Lys Glu
    210                 215                 220 aat gac aga att ttt gtt tct gta aca aat gag cac ttg ata gac atg     720
Asn Asp Arg Ile Phe Val Ser Val Thr Asn Glu His Leu Ile Asp Met
225                 230                 235                 240
```

```
gac cat gaa gcc agt ttt ttc ggg gcc ttt tta gtt ggc         759
Asp His Glu Ala Ser Phe Phe Gly Ala Phe Leu Val Gly
            245                 250
```

<210> SEQ ID NO 11
<211> LENGTH: 253
<212> TYPE: PRT
<213> ORGANISM: synthetic fusion

<400> SEQUENCE: 11

```
Met Ala Thr Gly Ser Arg Thr Ser Leu Leu Ala Phe Gly Leu Leu
 1               5                  10                  15

Cys Leu Pro Trp Leu Gln Glu Gly Ser Ala Thr Ser Ser Asp Arg Met
                20                  25                  30

Lys Gln Ile Glu Asp Lys Ile Glu Ile Leu Ser Lys Ile Tyr His
            35                  40                  45

Ile Glu Asn Glu Ile Ala Arg Ile Lys Lys Leu Ile Gly Glu Arg Thr
        50                  55                  60

Arg Ser Thr Ser Glu Glu Thr Ile Ser Thr Val Gln Glu Lys Gln Gln
 65                 70                  75                  80

Asn Ile Ser Pro Leu Val Arg Glu Arg Gly Pro Gln Arg Val Ala Ala
                85                  90                  95

His Ile Thr Gly Thr Arg Gly Arg Ser Asn Thr Leu Ser Ser Pro Asn
            100                 105                 110

Ser Lys Asn Glu Lys Ala Leu Gly Arg Lys Ile Asn Ser Trp Glu Ser
        115                 120                 125

Ser Arg Ser Gly His Ser Phe Leu Ser Asn Leu His Leu Arg Asn Gly
    130                 135                 140

Glu Leu Val Ile His Glu Lys Gly Phe Tyr Tyr Ile Tyr Ser Gln Thr
145                 150                 155                 160

Tyr Phe Arg Phe Gln Glu Glu Ile Lys Glu Asn Thr Lys Asn Asp Lys
                165                 170                 175

Gln Met Val Gln Tyr Ile Tyr Lys Tyr Thr Ser Tyr Pro Asp Pro Ile
            180                 185                 190

Leu Leu Met Lys Ser Ala Arg Asn Ser Cys Trp Ser Lys Asp Ala Glu
        195                 200                 205

Tyr Gly Leu Tyr Ser Ile Tyr Gln Gly Gly Ile Phe Glu Leu Lys Glu
    210                 215                 220

Asn Asp Arg Ile Phe Val Ser Val Thr Asn Glu His Leu Ile Asp Met
225                 230                 235                 240

Asp His Glu Ala Ser Phe Phe Gly Ala Phe Leu Val Gly
                245                 250
```

<210> SEQ ID NO 12
<211> LENGTH: 768
<212> TYPE: DNA
<213> ORGANISM: synthetic fusion
<220> FEATURE:
<221> NAME/KEY: CDS
<222> LOCATION: (1)..(768)

<400> SEQUENCE: 12

```
atg gct cgg agg cta tgg atc ttg agc tta tta gcc gtg acc ttg acg      48
Met Ala Arg Arg Leu Trp Ile Leu Ser Leu Leu Ala Val Thr Leu Thr
 1               5                  10                  15 gtg gct ttg gcg gca cct tct cag aaa tcg aag cgc agg act agt tct      96
Val Ala Leu Ala Ala Pro Ser Gln Lys Ser Lys Arg Arg Thr Ser Ser
                20                  25                  30
```

-continued

```
gac cgt atg aaa cag ata gag gat aag atc gaa gag atc cta agt aag         144
Asp Arg Met Lys Gln Ile Glu Asp Lys Ile Glu Glu Ile Leu Ser Lys
         35                  40                  45 att tat cat ata gag aat gaa atc gcc cgt atc aaa aag ctg att ggc         192
Ile Tyr His Ile Glu Asn Glu Ile Ala Arg Ile Lys Lys Leu Ile Gly
 50                  55                  60 gag cgg act aga tct acc tct gag gaa acc att tct aca gtt caa gaa         240
Glu Arg Thr Arg Ser Thr Ser Glu Glu Thr Ile Ser Thr Val Gln Glu
 65                  70                  75                  80 aag caa caa aat att tct ccc cta gtg aga gaa aga ggt cct cag aga         288
Lys Gln Gln Asn Ile Ser Pro Leu Val Arg Glu Arg Gly Pro Gln Arg
                 85                  90                  95 gta gca gct cac ata act ggg acc aga gga aga agc aac aca ttg tct         336
Val Ala Ala His Ile Thr Gly Thr Arg Gly Arg Ser Asn Thr Leu Ser
            100                 105                 110 tct cca aac tcc aag aat gaa aag gct ctg ggc cgc aaa ata aac tcc         384
Ser Pro Asn Ser Lys Asn Glu Lys Ala Leu Gly Arg Lys Ile Asn Ser
        115                 120                 125 tgg gaa tca tca agg agt ggg cat tca ttc ctg agc aac ttg cac ttg         432
Trp Glu Ser Ser Arg Ser Gly His Ser Phe Leu Ser Asn Leu His Leu
130                 135                 140 agg aat ggt gaa ctg gtc atc cat gaa aaa ggg ttt tac tac atc tat         480
Arg Asn Gly Glu Leu Val Ile His Glu Lys Gly Phe Tyr Tyr Ile Tyr
145                 150                 155                 160 tcc caa aca tac ttt cga ttt cag gag gaa ata aaa gaa aac aca aag         528
Ser Gln Thr Tyr Phe Arg Phe Gln Glu Glu Ile Lys Glu Asn Thr Lys
                165                 170                 175 aac gac aaa caa atg gtc caa tat att tac aaa tac aca agt tat cct         576
Asn Asp Lys Gln Met Val Gln Tyr Ile Tyr Lys Tyr Thr Ser Tyr Pro
            180                 185                 190 gac cct ata ttg ttg atg aaa agt gct aga aat agt tgt tgg tct aaa         624
Asp Pro Ile Leu Leu Met Lys Ser Ala Arg Asn Ser Cys Trp Ser Lys
        195                 200                 205 gat gca gaa tat gga ctc tat tcc atc tat caa ggg gga ata ttt gag         672
Asp Ala Glu Tyr Gly Leu Tyr Ser Ile Tyr Gln Gly Gly Ile Phe Glu
210                 215                 220 ctt aag gaa aat gac aga att ttt gtt tct gta aca aat gag cac ttg         720
Leu Lys Glu Asn Asp Arg Ile Phe Val Ser Val Thr Asn Glu His Leu
225                 230                 235                 240 ata gac atg gac cat gaa gcc agt ttt ttc ggg gcc ttt tta gtt ggc         768
Ile Asp Met Asp His Glu Ala Ser Phe Phe Gly Ala Phe Leu Val Gly
                245                 250                 255
```

<210> SEQ ID NO 13
<211> LENGTH: 256
<212> TYPE: PRT
<213> ORGANISM: synthetic fusion

<400> SEQUENCE: 13

```
Met Ala Arg Arg Leu Trp Ile Leu Ser Leu Leu Ala Val Thr Leu Thr
 1               5                  10                  15

Val Ala Leu Ala Ala Pro Ser Gln Lys Ser Lys Arg Arg Thr Ser Ser
            20                  25                  30

Asp Arg Met Lys Gln Ile Glu Asp Lys Ile Glu Glu Ile Leu Ser Lys
        35                  40                  45

Ile Tyr His Ile Glu Asn Glu Ile Ala Arg Ile Lys Lys Leu Ile Gly
    50                  55                  60

Glu Arg Thr Arg Ser Thr Ser Glu Glu Thr Ile Ser Thr Val Gln Glu
 65                  70                  75                  80
```

-continued

```
Lys Gln Gln Asn Ile Ser Pro Leu Val Arg Glu Arg Gly Pro Gln Arg
                 85                  90                  95

Val Ala Ala His Ile Thr Gly Thr Arg Gly Arg Ser Asn Thr Leu Ser
            100                 105                 110

Ser Pro Asn Ser Lys Asn Glu Lys Ala Leu Gly Arg Lys Ile Asn Ser
        115                 120                 125

Trp Glu Ser Ser Arg Ser Gly His Ser Phe Leu Ser Asn Leu His Leu
    130                 135                 140

Arg Asn Gly Glu Leu Val Ile His Glu Lys Gly Phe Tyr Tyr Ile Tyr
145                 150                 155                 160

Ser Gln Thr Tyr Phe Arg Phe Gln Glu Glu Ile Lys Glu Asn Thr Lys
                165                 170                 175

Asn Asp Lys Gln Met Val Gln Tyr Ile Tyr Lys Tyr Thr Ser Tyr Pro
            180                 185                 190

Asp Pro Ile Leu Leu Met Lys Ser Ala Arg Asn Ser Cys Trp Ser Lys
        195                 200                 205

Asp Ala Glu Tyr Gly Leu Tyr Ser Ile Tyr Gln Gly Gly Ile Phe Glu
    210                 215                 220

Leu Lys Glu Asn Asp Arg Ile Phe Val Ser Val Thr Asn Glu His Leu
225                 230                 235                 240

Ile Asp Met Asp His Glu Ala Ser Phe Phe Gly Ala Phe Leu Val Gly
                245                 250                 255

<210> SEQ ID NO 14
<211> LENGTH: 27
<212> TYPE: PRT
<213> ORGANISM: LZ peptide

<400> SEQUENCE: 14

Pro Asp Val Ala Ser Leu Arg Gln Gln Val Glu Ala Leu Gln Gly Gln
  1               5                  10                  15

Val Gln His Leu Gln Ala Ala Phe Ser Gln Tyr
                20                  25

<210> SEQ ID NO 15
<211> LENGTH: 34
<212> TYPE: PRT
<213> ORGANISM: LZ peptide

<400> SEQUENCE: 15

Asp Arg Met Lys Gln Ile Glu Asp Lys Ile Glu Ile Leu Ser Lys
  1               5                  10                  15

Ile Tyr His Ile Glu Asn Glu Ile Ala Arg Ile Lys Lys Leu Ile Gly
                20                  25                  30

Glu Arg

<210> SEQ ID NO 16
<211> LENGTH: 28
<212> TYPE: PRT
<213> ORGANISM: LZ peptide

<400> SEQUENCE: 16

Ser Leu Ala Ser Leu Arg Gln Gln Leu Glu Ala Leu Gln Gly Gln Leu
  1               5                  10                  15

Gln His Leu Gln Ala Ala Leu Ser Gln Leu Gly Glu
                20                  25

<210> SEQ ID NO 17
```

```
<211> LENGTH: 28
<212> TYPE: PRT
<213> ORGANISM: LZ peptide

<400> SEQUENCE: 17

Ser Ile Ala Ser Ile Arg Gln Gln Ile Glu Ala Ile Gln Gly Gln Ile
  1               5                  10                  15

Gln His Ile Gln Ala Ala Ile Ser Gln Ile Gly Glu
            20                  25

<210> SEQ ID NO 18
<211> LENGTH: 77
<212> TYPE: DNA
<213> ORGANISM: GH Leader

<400> SEQUENCE: 18
atggctacag gctcccggac gtccctgtcc tggcttttgg cctgctctgc ctgccctggc     60
ttcaagaggg cagtgca                                                    77

<210> SEQ ID NO 19
<211> LENGTH: 26
<212> TYPE: PRT
<213> ORGANISM: GH Leader

<400> SEQUENCE: 19

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala
            20                  25

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: artificial
      peptide

<400> SEQUENCE: 20

Cys Asp Cys Arg Gly Asp Cys Phe Cys
  1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: artificial
      peptide

<400> SEQUENCE: 21

Cys Asn Gly Arg Cys Val Ser Gly Cys Ala Gly Arg Cys
  1               5                  10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: artificial
      peptide

<400> SEQUENCE: 22

Asn Gly Arg Ala His Ala
  1               5
```

-continued

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: artificial
      peptide

<400> SEQUENCE: 23

Cys Val Leu Asn Gly Arg Met Glu Cys
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: artificial
      peptide

<400> SEQUENCE: 24

Cys Asn Gly Arg Cys
  1               5

<210> SEQ ID NO 25
<211> LENGTH: 20
<212> TYPE: PRT
<213> ORGANISM: Homo sapiens

<400> SEQUENCE: 25

Met Gly Thr Asp Thr Leu Leu Leu Trp Val Leu Leu Leu Trp Val Pro
  1               5                  10                  15

Gly Ser Thr Gly
             20
```

US 6,521,228 B1

ANTIBODIES DIRECTED AGAINST TRAIL

CROSS-REFERENCE TO RELATED APPLICATIONS

This application is a divisional of application Ser. No. 09/320,424, filed May 26, 1999, now U.S. Pat. No. 6,284,236, which is a continuation-in-part of application Ser. No. 09/190,046, filed Nov. 10, 1998, now abandoned, which is a continuation-in-part of application Ser. No. 09/048,641, filed Mar. 26, 1998, now abandoned, which is a continuation-in-part of application Ser. No. 08/670,354, filed Jun. 25, 1996, now U.S. Pat. No. 5,763,223, which is a continuation-in-part of application Ser. No. 08/548,368, filed Nov. 1, 1995, now abandoned, which is a continuation-in-part of application Ser. No. 08/496,632, filed Jun. 29, 1995, now abandoned.

BACKGROUND OF THE INVENTION

The programmed cell death known as apoptosis is distinct from cell death due to necrosis. Apoptosis occurs in embryogenesis, metamorphosis, endocrine-dependent tissue atrophy, normal tissue turnover, and death of immune thymocytes (induced through their antigen-receptor complex or by glucocorticoids) (Itoh et al., Cell 66:233, 1991). During maturation of T-cells in the thymus, T-cells that recognize self-antigens are destroyed through the apoptotic process, whereas others are positively selected. The possibility that some T-cells recognizing certain self epitopes (e.g., inefficiently processed and presented antigenic determinants of a given self protein) escape this elimination process and subsequently play a role in autoimmune diseases has been suggested (Gammon et al., Immunology Today 12:193, 1991).

A cell surface antigen known as Fas has been reported to mediate apoptosis and is believed to play a role in clonal deletion of self-reactive T-cells (Itoh et al., Cell 66:233, 1991; Watanabe-Fukunage et al., Nature 356:314, 1992). Cross-linking a specific monoclonal antibody to Fas has been reported to induce various cell lines to undergo apoptosis (Yonehara et al., J. Exp. Med., 169:1747, 1989; Trauth et al., Science, 245:301, 1989). However, under certain conditions, binding of a specific monoclonal antibody to Fas can have a costimulatory effect on freshly isolated T cells (Alderson et al., J. Exp. Med. 178:2231, 1993).

DNAs encoding a rat Fas ligand (Suda et al., Cell, 75:1169, 1993) and a human Fas ligand (Takahashi et al., International Immunology 6:1567, 1994) have been isolated. Binding of the Fas ligand to cells expressing Fas antigen has been demonstrated to induce apoptosis (Suda et al., supra, and Takahashi et al., supra).

Investigation into the existence and identity of other molecule(s) that play a role in apoptosis is desirable. Identifying such molecules would provide an additional means of regulating apoptosis, as well as providing further insight into the development of self-tolerance by the immune system and the etiology of autoimmune diseases.

SUMMARY OF THE INVENTION

The present invention provides a novel cytokine protein, as well as isolated DNA encoding the cytokine and expression vectors comprising the isolated DNA. Properties of the novel cytokine, which is a member of the tumor necrosis factor (TNF) family of ligands, include the ability to induce apoptosis of certain types of target cells. This protein thus is designated TNF Related Apoptosis Inducing Ligand (TRAIL). Among the types of cells that are killed by contact with TRAIL are cancer cells such as leukemia, lymphoma, and melanoma cells, and cells infected with a virus.

A method for producing TRAIL polypeptides involves culturing host cells transformed with a recombinant expression vector that contains TRAIL-encoding DNA under conditions appropriate for expression of TRAIL, then recovering the expressed TRAIL polypeptide from the culture. Antibodies directed against TRAIL polypeptides are also provided.

BRIEF DESCRIPTION OF THE DRAWINGS

FIG. 3 depicts a particular fusion protein encoded by an expression vector of the present invention. The fusion protein comprises (from N- to C-terminus) a growth hormone-derived leader sequence (SEQ ID NO:19), followed by a tripeptide encoded by an oligonucleotide employed in vector construction, a leucine zipper peptide (SEQ ID NO:15), a tripeptide encoded by an oligonucleotide employed in vector construction, and a soluble human TRAIL polypeptide (amino acids 95 to 281 of SEQ ID NO:2). A DNA sequence encoding the fusion protein, and the amino acid sequence of the fusion protein, are presented in SEQ ID NO:10 and 11, respectively.

FIG. 4 depicts a fusion protein encoded by another expression vector of the present invention, comprising (from N- to C-terminus) a cytomegalovirus-derived leader sequence (amino acids 1 to 29 of SEQ ID NO:9), followed by a tripeptide encoded by an oligonucleotide employed in vector construction (amino acids 30 to 32 of SEQ ID NO:9), a leucine zipper peptide (SEQ ID NO:15), a tripeptide encoded by an oligonucleotide employed in vector construction, and a soluble human TRAIL polypeptide (amino acids 95 to 281 of SEQ ID NO:2). A DNA sequence encoding the fusion protein, and the amino acid sequence of the fusion protein, are presented in SEQ ID NO:12 and 13, respectively.

DETAILED DESCRIPTION OF THE INVENTION

Figure 1:
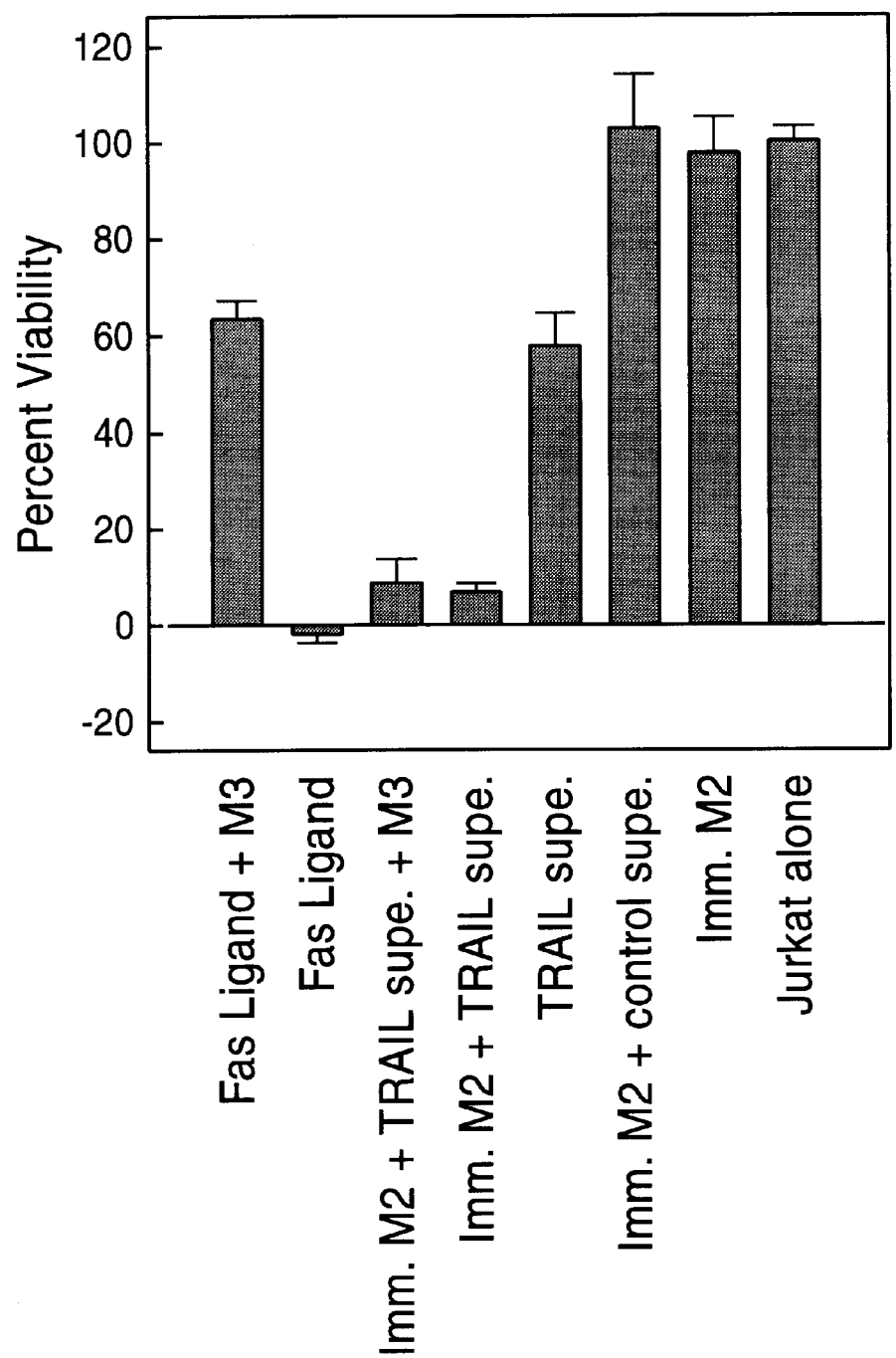
FIG. 1 presents the results of an assay described in example 8. The assay demonstrated that a soluble human TRAIL polypeptide induced death of Jurkat cells, which are a leukemia cell line.

A novel protein designated TRAIL is provided herein, along with DNA encoding TRAIL and recombinant expression vectors comprising TRAIL DNA. A method for producing recombinant TRAIL polypeptides involves cultivating host cells transformed with the recombinant expression vectors under conditions appropriate for expression of TRAIL, and recovering the expressed TRAIL.

The present invention also provides antibodies that specifically bind TRAIL proteins. In one embodiment, the antibodies are monoclonal antibodies.

The TRAIL protein induces apoptosis of certain types of target cells, such as transformed cells that include but are not limited to cancer cells and virally-infected cells. As demonstrated in examples 5, 8, 9, and 10 below, TRAIL induced apoptosis of human leukemia, lymphoma, and melanoma cell lines. Among the uses of TRAIL is use in killing cancer cells. TRAIL finds further use in treatment of viral infections. Infection with cytomegalovirus (CMV) rendered human fibroblasts susceptible to apoptosis when contacted with TRAIL, whereas uninfected fibroblasts were not killed through contact with TRAIL (see example 11).

Isolation of a DNA encoding human TRAIL is described in example 1 below. The nucleotide sequence of the human TRAIL DNA isolated in example 1 is presented in SEQ ID NO:1, and the amino acid sequence encoded thereby is presented in SEQ ID NO:2. This human TRAIL protein comprises an N-terminal cytoplasmic domain (amino acids 1–18), a transmembrane region (amino acids 19–38), and an extracellular domain (amino acids 39–281). The extracellular domain contains a receptor-binding region.

E. coli strain DH10B cells transformed with a recombinant vector containing this human TRAIL DNA were deposited with the American Type Culture Collection on Jun. 14, 1995, and assigned accession no. 69849. The deposit was made under the terms of the Budapest Treaty. The recombinant vector in the deposited strain is the expression vector pDC409 (described in example 5). The vector was digested with SalI and NotI, and human TRAIL DNA that includes the entire coding region shown in SEQ ID NO:1 was ligated into the vector.

DNA encoding a second human TRAIL protein was isolated as described in example 2. The nucleotide sequence of this DNA is presented in SEQ ID NO:3, and the amino acid sequence encoded thereby is presented in SEQ ID NO:4. The encoded protein comprises an N-terminal cytoplasmic domain (amino acids 1–18), a transmembrane region (amino acids 19–38), and an extracellular domain (amino acids 39–101).

The DNA of SEQ ID NO:3 lacks a portion of the DNA of SEQ ID NO:1, and is thus designated the human TRAIL deletion variant (huTRAILdv) clone. Nucleotides 18 through 358 of SEQ ID NO:1 are identical to nucleotides 8 through 348 of the huTRAILdv DNA of SEQ ID NO:3. Nucleotides 359 through 506 of SEQ ID NO:1 are missing from the cloned DNA of SEQ ID NO:3. The deletion causes a shift in the reading frame, which results in an in-frame stop codon after amino acid 101 of SEQ ID NO:4. The DNA of SEQ ID NO:3 thus encodes a truncated protein. Amino acids 1 through 90 of SEQ ID NO:2 are identical to amino acids 1 through 90 of SEQ ID NO:4. However, due to the deletion, the C-terminal portion of the huTRAILdv protein (amino acids 91 through 101 of SEQ ID NO:4) differs from the residues in the corresponding positions in SEQ ID NO:2. In contrast to the full length huTRAIL protein, the truncated huTRAILdv protein does not exhibit the ability to induce apoptosis of the T cell leukemia cells of the Jurkat cell line.

DNA encoding a mouse TRAIL protein has also been isolated, as described in example 3. The nucleotide sequence of this DNA is presented in SEQ ID NO:5 and the amino acid sequence encoded thereby is presented in SEQ ID NO:6. The encoded protein comprises an N-terminal cytoplasmic domain (amino acids 1–17), a transmembrane region (amino acids 18–38), and an extracellular domain (amino acids 39–291). This mouse TRAIL is 64% identical to the human TRAIL of SEQ ID NO:2 at the amino acid level. The coding region of the mouse TRAIL nucleotide sequence is 75% identical to the coding region of the human nucleotide sequence of SEQ ID NO:1.

One embodiment of the present invention is directed to human TRAIL protein characterized by the N-terminal amino acid sequence MetAlaMetMetGluValGlnGly GlyProSerLeuGlyGlnThr (amino acids 1–15 of SEQ ID NOS:2 and 4). Mouse TRAIL proteins characterized by the N-terminal amino acid sequence MetProSerSerGlyAla LeuLysAspLeuSerPheSerGlnHis (amino acids 1–15 of SEQ ID NO:6) are also provided herein.

The TRAIL of the present invention is distinct from the protein known as Fas ligand (Suda et al., Cell, 75:1169, 1993; Takahashi et al., International Immunology 6:1567, 1994). Fas ligand induces apoptosis of certain cell types, via the receptor known as Fas. As demonstrated in example 5, TRAIL-induced apoptosis of target cells is not mediated through Fas. The human TRAIL amino acid sequence of SEQ ID NO:2 is about 20% identical to the human Fas ligand amino acid sequence that is presented in Takahashi et al., supra. The extracellular domain of human TRAIL is about 28.4% identical to the extracellular domain of human Fas ligand.

The amino acid sequences disclosed herein reveal that TRAIL is a member of the TNF family of ligands (Smith et al. Cell, 73:1349, 1993; Suda et al., Cell, 75:1169, 1993; Smith et al., Cell, 76:959, 1994). The percent identities between the human TRAIL extracellular domain amino acid sequence and the amino acid sequence of the extracellular domain of other proteins of this family are as follows: 28.4% with Fas ligand, 22.4% with lymphotoxin-β, 22.9% with TNF-α, 23.1% with TNF-β, 22.1% with CD30 ligand, and 23.4% with CD40 ligand.

TRAIL was tested for ability to bind receptors of the TNF-R family of receptors. The binding analysis was conducted using the slide autoradiography procedure of Gearing et al. (EMBO J. 8:3667, 1989). The analysis revealed no detectable binding of human TRAIL to human CD30, CD40, 4-1BB, OX40, TNF-R (p80 form), CD27, or LTβR (also known as TNFR-RP). The results in example 5 indicate that human TRAIL does not bind human Fas.

The TRAIL polypeptides of the present invention include polypeptides having amino acid sequences that differ from, but are highly homologous to, those presented in SEQ ID NOS:2 and 6. Examples include, but are not limited to, homologs derived from other mammalian species, variants (both naturally occurring variants and those generated by recombinant DNA technology), and TRAIL fragments that retain a desired biological activity. Such polypeptides exhibit a biological activity of the TRAIL proteins of SEQ ID NOS:2 and 6, and preferably comprise an amino acid sequence that is at least 80% identical (most preferably at least 90% identical) to the amino acid sequence presented in SEQ ID NO:2 or SEQ ID NO:6. These embodiments of the present invention are described in more detail below.

Conserved sequences located in the C-terminal portion of proteins in the TNF family are identified in Smith et al. (Cell, 73:1349, 1993, see page 1353 and FIG. 6); Suda et al. (Cell, 75:1169, 1993, see FIG. 7); Smith et al. (Cell, 76:959, 1994, see FIG. 3); and Goodwin et al. (Eur. J. Immunol., 23:2631, 1993, see FIG. 7 and pages 2638–39), hereby incorporated by reference. Among the amino acids in the human TRAIL protein that are conserved (in at least a majority of TNF family members) are those in positions 124–125 (AH), 136 (L), 154 (W), 169 (L), 174 (L), 180 (G), 182 (Y), 187 (Q), 190 (F), 193 (Q), and 275–276 (FG) of SEQ ID NO:2. Another structural feature of TRAIL is a spacer region between the C-terminus of the transmembrane region and the portion of the extracellular domain that is believed to be most important for biological activity. This spacer region, located at the N-terminus of the extracellular domain, consists of amino acids 39 through 94 of SEQ ID NO:2. Analogous spacers are found in other family members, e.g., CD40 ligand. Amino acids 138 through 153 correspond to a loop between the β sheets of the folded (three dimensional) human TRAIL protein.

Provided herein are membrane-bound TRAIL proteins (comprising a cytoplasmic domain, a transmembrane region, and an extracellular domain) as well as TRAIL fragments that retain a desired biological property of the full length TRAIL protein. In one embodiment, TRAIL fragments are soluble TRAIL polypeptides comprising all or part of the extracellular domain, but lacking the transmembrane region that would cause retention of the polypeptide on a cell membrane. Soluble TRAIL proteins are capable of being secreted from the cells in which they are expressed. Advantageously, a heterologous signal peptide is fused to the N-terminus such that the soluble TRAIL is secreted upon expression.

Soluble TRAIL may be identified (and distinguished from its non-soluble membrane-bound counterparts) by separating intact cells which express the desired protein from the culture medium, e.g., by centrifugation, and assaying the medium (supernatant) for the presence of the desired protein. The presence of TRAIL in the medium indicates that the protein was secreted from the cells and thus is a soluble form of the TRAIL protein. Naturally-occurring soluble forms of TRAIL are encompassed by the present invention.

The use of soluble forms of TRAIL is advantageous for certain applications. Purification of the proteins from recombinant host cells is facilitated, since the soluble proteins are secreted from the cells. Further, soluble proteins are generally more suitable for intravenous administration.

Examples of soluble TRAIL polypeptides are those containing the entire extracellular domain (e.g., amino acids 39 to 281 of SEQ ID NO:2 or amino acids 39 to 291 of SEQ ID NO:6). Fragments of the extracellular domain that retain a desired biological activity are also provided. Such fragments advantageously include regions of TRAIL that are conserved in proteins of the TNF family of ligands, as described above.

Additional examples of soluble TRAIL polypeptides are those lacking not only the cytoplasmic domain and transmembrane region, but also all or part of the above-described spacer region. Soluble human TRAIL polypeptides thus include, but are not limited to, polypeptides comprising amino acids x to 281, wherein x represents any of the amino acids in positions 39 through 95 of SEQ ID NO:2. In the embodiment in which residue 95 is the N-terminal amino acid, the entire spacer region has been deleted.

TRAIL fragments, including soluble polypeptides, may be prepared by any of a number of conventional techniques. A DNA sequence encoding a desired TRAIL fragment may be subcloned into an expression vector for production of the TRAIL fragment. The TRAIL-encoding DNA sequence advantageously is fused to a sequence encoding a suitable leader or signal peptide. The desired TRAIL-encoding DNA fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to faciliate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et al., eds., Academic Press, Inc. (1990).

As will be understood by the skilled artisan, the transmembrane region of each TRAIL protein discussed above is identified in accordance with conventional criteria for identifying that type of hydrophobic domain. The exact boundaries of a transmembrane region may vary slightly (most likely by no more than five amino acids on either end) from those presented above. Computer programs useful for identifying such hydrophobic regions in proteins are available.

The TRAIL DNA of the present invention includes cDNA, chemically synthesized DNA, DNA isolated by PCR, genomic DNA, and combinations thereof. Genomic TRAIL DNA may be isolated by hybridization to the TRAIL cDNA disclosed herein using standard techniques. RNA transcribed from the TRAIL DNA is also encompassed by the present invention.

A search of the NCBI databank identified five expressed sequence tags (ESTs) having regions of identity with TRAIL DNA. These ESTs (NCBI accession numbers T90422, T82085, T10524, R31020, and Z36726) are all human cDNA fragments. The NCBI records do not disclose any polypeptide encoded by the ESTs, and do not indicate what the reading frame, if any, might be. However, even if the knowledge of the reading frame revealed herein by disclosure of complete TRAIL coding regions is used to express the ESTs, none of the encoded polypeptides would have the apoptosis-inducing property of the presently-claimed TRAIL polypeptides. In other words, if each of the five ESTs were inserted into expression vectors downstream from an initiator methionine codon, in the reading frame elucidated herein, none of the resulting expressed polypeptides would contain a sufficient portion of the extracellular domain of TRAIL to induce apoptosis of Jurkat cells.

Certain embodiments of the present invention provide isolated DNA comprising a nucleotide sequence selected from the group consisting of nucleotides 88 to 933 of SEQ ID NO:1 (human TRAIL coding region); nucleotides 202 to 933 of SEQ ID NO:1 (encoding the human TRAIL extracellular domain); nucleotides 47 to 922 of SEQ ID NO:5 (mouse TRAIL coding region); and nucleotides 261 to 922 of SEQ ID NO:5 (encoding the mouse TRAIL extracellular domain). DNAs encoding biologically active fragments of the proteins of SEQ ID NOS:2 and 6 are also provided. Further embodiments include sequences comprising nucleotides 370 to 930 of SEQ ID NO:1 and nucleotides 341 to 919 of SEQ ID NO:5, which encode the particular human and murine soluble TRAIL polypeptides, respectively, described in example 7.

Due to degeneracy of the genetic code, two DNA sequences may differ, yet encode the same amino acid sequence. The present invention thus provides isolated DNA sequences encoding biologically active TRAIL, selected from DNA comprising the coding region of a native human or murine TRAIL CDNA, or fragments thereof, and DNA which is degenerate as a result of the genetic code to the native TRAIL DNA sequence.

Also provided herein are purified TRAIL polypeptides, both recombinant and non-recombinant. Variants and derivatives of native TRAIL proteins that retain a desired biological activity are also within the scope of the present invention. In one embodiment, the biological activity of an TRAIL variant is essentially equivalent to the biological activity of a native TRAIL protein. One desired biological activity of TRAIL is the ability to induce death of Jurkat cells. Assay procedures for detecting apoptosis of target cells are well known. DNA laddering is among the characteristics of cell death via apoptosis, and is recognized as one of the observable phenomena that distinguish apoptotic cell death from necrotic cell death. Examples of assay techniques suitable for detecting death or apoptosis of target cells include those described in examples 5 and 8 to 11. Another property of TRAIL is the ability to bind to Jurkat cells.

TRAIL variants may be obtained by mutations of native TRAIL nucleotide sequences, for example. A TRAIL variant, as referred to herein, is a polypeptide substantially homologous to a native TRAIL, but which has an amino acid sequence different from that of native TRAIL because of one or a plurality of deletions, insertions or substitutions. TRAIL-encoding DNA sequences of the present invention encompass sequences that comprise one or more additions, deletions, or substitutions of nucleotides when compared to a native TRAIL DNA sequence, but that encode an TRAIL protein that is essentially biologically equivalent to a native TRAIL protein.

The variant amino acid or DNA sequence preferably is at least 80% identical to a native TRAIL sequence, most preferably at least 90% identical. The degree of homology (percent identity) between a native and a mutant sequence may be determined, for example, by comparing the two sequences using computer programs commonly employed for this purpose. One suitable program is the GAP computer program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines identity as the number of aligned symbols (i.e., nucleotides or amino acids) which are identical, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Techniques for making such alterations include those disclosed by Walder et al. (*Gene* 42:133, 1986); Bauer et al. (*Gene* 37:73, 1985); Craik (*BioTechniques, Jan.* 12–19, 1985); Smith et al. (*Genetic Engineering: Principles and Methods*, Plenum Press, 1981); and U.S. Pat. Nos. 4,518,584 and 4,737,462, which are incorporated by reference herein.

Variants may comprise conservatively substituted sequences, meaning that one or more amino acid residues of a native TRAIL polypeptide are replaced by different residues, but that the conservatively substituted TRAIL polypeptide retains a desired biological activity that is essentially equivalent to that of a native TRAIL polypeptide. Examples of conservative substitutions include substitution of amino acids that do not alter the secondary and/or tertiary structure of TRAIL. Other examples involve substitution of amino acids outside of the receptor-binding domain, when the desired biological activity is the ability to bind to a receptor on target cells and induce apoptosis of the target cells. A given amino acid may be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. TRAIL polypeptides comprising conservative amino acid substitutions may be tested in one of the assays described herein to confirm that a desired biological activity of a native TRAIL is retained. DNA sequences encoding TRAIL polypeptides that contain such conservative amino acid substitutions are encompassed by the present invention.

Conserved amino acids located in the C-terminal portion of proteins in the TNF family, and believed to be important for biological activity, have been identified. These conserved sequences are discussed in Smith et al. (*Cell*, 73:1349, 1993, see page 1353 and FIG. 6); Suda et al. (*Cell*, 75:1169, 1993, see FIG. 7); Smith et al. (*Cell*, 76:959, 1994, see FIG. 3); and Goodwin et al. (*Eur. J. Immunol.*, 23:2631, 1993, see FIG. 7 and pages 2638–39). Advantageously, the conserved amino acids are not altered when generating conservatively substituted sequences. If altered, amino acids found at equivalent positions in other members of the TNF family are substituted.

TRAIL also may be modified to create TRAIL derivatives by forming covalent or aggregative conjugates with other chemical moieties, such as glycosyl groups, lipids, phosphate, acetyl groups and the like. Covalent derivatives of TRAIL may be prepared by linking the chemical moieties to functional groups on TRAIL amino acid side chains or at the N-terminus or C-terminus of a TRAIL polypeptide or the extracellular domain thereof. Other derivatives of TRAIL within the scope of this invention include covalent or aggregative conjugates of TRAIL or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a TRAIL polypeptide. The signal or leader peptide co-translationally or post-translationally directs transfer of the conjugate from its site of synthesis to a site inside or outside of the cell membrane or cell wall.

TRAIL polypeptide fusions can comprise peptides added to facilitate purification and identification of TRAIL. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:7), which is highly antigenic and provides an epitope reversibly bound by a specific monoclonal antibody, thus enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in E. coli.

A murine hybridoma designated 4E11 produces a monoclonal antibody that binds the peptide DYKDDDDK (SEQ ID NO:7) in the presence of certain divalent metal cations (as described in U.S. Pat. No. 5,011,912), and has been deposited with the American Type Culture Collection under accession no HB 9259. Expression systems useful for producing recombinant proteins fused to the FLAG® peptide, as well as monoclonal antibodies that bind the peptide and are useful in purifying the recombinant proteins, are available from Eastman Kodak Company, Scientific Imaging Systems, New Haven, Conn.

The present invention further includes TRAIL polypeptides with or without associated native-pattern glycosylation. TRAIL expressed in yeast or mammalian expression systems may be similar to or significantly different from a native TRAIL polypeptide in molecular weight and glycosylation pattern, depending upon the choice of expression system. Expression of TRAIL polypeptides in bacterial expression systems, such as E. coli, provides non-glycosylated molecules.

Glycosylation sites in the TRAIL extracellular domain can be modified to preclude glycosylation while allowing expression of a homogeneous, reduced carbohydrate analog using yeast or mammalian expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. Known procedures for inactivating N-glycosylation sites in proteins include those described in U.S. Pat. No. 5,071,972 and EP 276,846. A potential N-glycosylation site is found at positions 109–111 in the human protein of SEQ ID NO:2 and at positions 52–54 in the murine protein of SEQ ID NO:6.

Alternatively, known procedures such as mutagenesis may be employed to add glycosylation sites to TRAIL, thereby promoting an increase in the carbohydrate moieties attached to TRAIL. Such an approach may be taken when slowing the clearance of TRAIL from the body following in vivo administration is desired, for example.

In another example, sequences encoding Cys residues that are not essential for biological activity can be altered to cause the Cys residues to be deleted or replaced with other amino acids, preventing formation of incorrect intramolecular disulfide bridges upon renaturation. Cysteine residues are found in the human TRAIL protein of SEQ ID NO:2 at positions 16, 30, 56, 77, and 230; and in the murine TRAIL protein of SEQ ID NO:6 at positions 22, 60, 81, and 240.

Among the soluble human TRAIL polypeptides disclosed herein are fragments of the extracellular domain that lack the spacer region, as described above. Such spacer-deleted soluble TRAIL polypeptides include only one cysteine, corresponding to the residue at position 230 of SEQ ID NO:2. Thus, any disulfide bonds forming from the Cys-230 residue would be intermolecular, joining two such soluble TRAIL polypeptides. In the fusion protein of FIG. 3 (SEQ ID NO:11), the TRAIL polypeptide moiety comprises only one cysteine, at position 202 (which corresponds to the cysteine residue at position 230 in the full length human TRAIL sequence of SEQ ID NO:2). In the fusion protein of FIG. 4 (SEQ ID NO:13), the TRAIL polypeptide comprises only one cysteine, at position 205 (which corresponds to the Cys-230 residue in SEQ ID NO:2).

One embodiment of the invention is directed to a TRAIL polypeptide (or fusion protein comprising a TRAIL polypeptide), in which the cysteine residue corresponding to the cysteine at position 230 in SEQ ID NO:2 is deleted or substituted, in order to prevent formation of disulfide bonds that involve the Cys-230 residue. If substituted, cysteine may be replaced by any suitable amino acid, whereby a desired biological activity of TRAIL is maintained. Examples include, but are not limited to, serine, alanine, glycine, or valine. Altering the number of cysteine residues to manipulate oligomer formation is discussed further below.

Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Potential KEX2 protease processing sites are found at positions 89–90 and 149–150 in the protein of SEQ ID NO:2, and at positions 85–86, 135–136, and 162–163 in the protein of SEQ ID NO:6.

Naturally occurring TRAIL variants are also encompassed by the present invention. Examples of such variants are proteins that result from alternative mRNA splicing events (since TRAIL is encoded by a multi-exon gene) or from proteolytic cleavage of the TRAIL protein, wherein a desired biological activity is retained. Alternative splicing of MRNA may yield a truncated but biologically active TRAIL protein, such as a naturally occurring soluble form of the protein, for example. Variations attributable to proteolysis include, for example, differences in the N- or C-termini upon expression in different types of host cells, due to proteolytic removal of one or more terminal amino acids from the TRAIL protein. In addition, proteolytic cleavage may release a soluble form of TRAIL from a membrane-bound form of the protein. Allelic variants are also encompassed by the present invention.

Also provided herein are conjugates or fusion proteins comprising a TRAIL polypeptide and a tumor-targeting moiety. Such embodiments may be employed in cancer treatment, for example. The TRAIL component may be any of the various forms of TRAIL disclosed herein, with one example being a soluble TRAIL polypeptide. Oligomers comprising such fusion proteins also are contemplated. The conjugates or fusion proteins may additionally comprise other components of TRAIL-containing fusions, compositions, and the like that are described herein. Examples of such other components include, but are not limited to, leucine zipper peptides.

The tumor-targeting moiety may be any compound that enhances delivery of TRAIL to a tumor. Such compounds include, but are not limited to, compounds that selectively bind to cancer cells compared with normal cells, specifically bind to a particular type of cancer that is to be treated, or enhance penetration into solid tumors. In one embodiment, the tumor-targeting moiety is a peptide.

Examples of tumor-targeting peptides are described in Arap et al. (*Science* 279:377, Jan. 16, 1998), and Pasqualini et al. (*Nature Biotechnology* 15:542, June 1997), which are hereby incorporated by reference in their entirety. Arap et al. and Pasqualini et al. report studies of peptides that "home" to tumors, selectively binding to tumor vessels and/or to tumor cells. The tripeptides Arg-Gly-Asp, Asn-Gly-Arg and Gly-Ser-Leu, or peptides comprising such tripeptide sequences, are contemplated herein for use as tumor targeting moieties as components of TRAIL fusion proteins.

Arap et al. and Pasqualini et al., supra, disclose that peptides comprising the sequence Arg-Gly-Asp (RGD) bind to integrins, including but not limited to $\alpha_v$ integrins. Such integrins have been detected in tumor vasculature and on a number of tumor cell types.

Arap et al. additionally disclose that peptides comprising the tripeptide Asn-Gly-Arg or Gly-Ser-Leu selectively bind to tumors. Among the peptides studied by Arap et al. are the RGD-containing peptide CDCRGDCFC (SEQ ID NO:20), and the NGR-containing peptides CNGRCVSGCAGRC (SEQ ID NO:21), NGRAHA (SEQ ID NO:22), CVLN-GRMEC (SEQ ID NO:23), and CNGRC (SEQ ID NO:24).

One type of fusion protein provided herein comprises a TRAIL polypeptide and a peptide that binds an integrin associated with a tumor. Such integrin may be expressed on tumor cells or tumor vessels, for example. An example of an integrin is an $\alpha_v$ integrin. Arap et al., supra, note that human $\alpha_v$ integrins are selectively expressed in human tumor blood vessels.

Oligomers

The present invention encompasses TRAIL polypeptides in the form of oligomers, such as dimers, trimers, or higher oligomers. Oligomers may be formed by disulfide bonds between cysteine residues on different TRAIL polypeptides, or by non-covalent interactions between TRAIL polypeptide chains, for example. In other embodiments, oligomers comprise from two to four TRAIL polypeptides joined via covalent or non-covalent interactions between peptide moieties fused to the TRAIL polypeptides. Such peptides may be peptide linkers (spacers), or peptides that have the property of promoting oligomerization. Leucine zippers and certain polypeptides derived from antibodies are among the peptides that can promote oligomerization of TRAIL polypeptides attached thereto, as described in more detail below. The TRAIL polypeptides preferably are soluble.

Preparation of fusion proteins comprising heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:667, 1990); and Hollenbaugh and Aruffo ("Construction of Immunoglobulin Fusion Proteins", in *Current Protocols in Immunology*, Supplement 4, pages 10.19.1–10.19.11, 1992), hereby incorporated by reference. In one embodiment of the invention, an TRAIL dimer is created by fusing TRAIL to an Fc region polypeptide derived from an antibody. The term "Fc polypeptide" includes native and mutein forms, as well as truncated Fc polypeptides containing the hinge region that promotes dimerization. The Fc polypeptide preferably is fused to a soluble TRAIL (e.g., comprising only the extracellular domain).

A gene fusion encoding the TRAIL/Fc fusion protein is inserted into an appropriate expression vector. In one embodiment, the Fc polypeptide is fused to the N-terminus of a soluble TRAIL polypeptide. The TRAIL/Fc fusion proteins are allowed to assemble much like antibody molecules, whereupon interchain disulfide bonds form between the Fc polypeptides, yielding divalent TRAIL. In other embodiments, TRAIL may be substituted for the variable portion of an antibody heavy or light chain. If fusion proteins are made with both heavy and light chains of an antibody, it is possible to form an TRAIL oligomer with as many as four TRAIL extracellular regions.

One suitable Fc polypeptide is the native Fc region polypeptide derived from a human IgG1, which is described in PCT application WO 93/10151, hereby incorporated by reference. Another useful Fc polypeptide is the Fc mutein described in U.S. Pat. No. 5,457,035. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

Alternatively, oligomeric TRAIL may comprise two or more soluble TRAIL polypeptides joined through peptide linkers. Examples include those peptide linkers described in U.S. Pat. No. 5,073,627 (hereby incorporated by reference). Fusion proteins comprising multiple TRAIL polypeptides separated by peptide linkers may be produced using conventional recombinant DNA technology.

Another method for preparing oligomeric TRAIL polypeptides involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

Leucine zippers were originally identified in several DNA-binding proteins (Landschulz et al., *Science* 240:1759, 1988). Zipper domain is a term used to refer to a conserved peptide domain present in these (and other) proteins, which is responsible for oligomerization of the proteins. The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains preferentially form a heterodimer (O'Shea et al., *Science* 245:646, 1989; Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils. (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated $(abcdefg)_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek et al., *Int. J. Peptide Res.* 38:229, 1991). Lovejoy et al. recently reported the synthesis of a triple-stranded α-helical bundle in which the helices run up-up-down (*Science* 259:1288, 1993). Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al. (*Science* 262:1401, Nov. 26, 1993).

Several studies have indicated that conservative amino acids may be substituted for individual leucine residues with minimal decrease in the ability to dimerize; multiple changes, however, usually result in loss of this ability (Landschulz et al., *Science* 243:1681, 1989; Turner and Tjian, *Science* 243:1689, 1989; Hu et al., *Science* 250:1400, 1990). van Heekeren et al. reported that a number of different amino residues can be substituted for the leucine residues in the zipper domain of GCN4, and further found that some GCN4 proteins containing two leucine substitutions were weakly active (*Nucl. Acids Res.* 20:3721, 1992). Mutation of the first and second heptadic leucines of the zipper domain of the measles virus fusion protein (MVF) did not affect syncytium formation (a measure of virally-induced cell fusion); however, mutation of all four leucine residues prevented fusion completely (Buckland et al., *J. Gen. Virol.* 73:1703, 1992). None of the mutations affected the ability of MVF to form a tetramer.

Examples of leucine zipper domains suitable for producing soluble oligomeric TRAIL proteins include, but are not limited to, those described in PCT application WO 94/10308 and in U.S. Pat. No. 5,716,805, hereby incorporated by reference. Recombinant fusion proteins comprising a soluble TRAIL polypeptide, fused to a peptide that dimerizes or trimerizes in solution, are expressed in suitable host cells, and the resulting soluble oligomeric TRAIL is recovered from the culture supernatant. DNA encoding such fusion proteins is provided herein.

Certain members of the TNF family of proteins are believed to exist in trimeric form (Beutler and Huffel, *Science* 264:667, 1994; Banner et al., *Cell* 73:431, 1993). Thus, trimeric TRAIL may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, 1994) and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO:14).

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg (residues 2 to 34 of SEQ ID NO:15), as described in U.S. Pat. No. 5,716,805. In an alternative embodiment, the peptide lacks the N-terminal Arg residue, thus comprising residues 3 to 34 of SEQ ID NO:15. In another embodiment, an N-terminal Asp residue is added, such that the peptide comprises the sequence Asp Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg (SEQ ID NO:15).

Yet another example of a suitable leucine zipper peptide comprises the amino acid sequence Ser Leu Ala Ser Leu Arg Gln Gln Leu Glu Ala Leu Gln Gly Gln Leu Gln His Leu Gln Ala Ala Leu Ser Gln Leu Gly Glu (SEQ ID NO:16). In an alternative peptide, the leucine residues in the foregoing sequence are replaced with isoleucine: Ser Ile Ala Ser Ile Arg Gln Gln Ile Glu Ala Ile Gln Gly Gln Ile Gln His Ile Gln Ala Ala Ile Ser Gln Ile Gly Glu (SEQ ID NO:17). Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences.

Other peptides derived from naturally occurring trimeric proteins may be employed in preparing trimeric TRAIL. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

As described in example 7, a soluble Flag®-TRAIL polypeptide expressed in CV-1/EBNA cells spontaneously formed oligomers believed to be a mixture of dimers and trimers. The cytotoxic effect of this soluble Flag®-TRAIL in the assay of example 8 was enhanced by including an anti-Flag® antibody, possibly because the antibody facilitated cross-linking of TRAIL/receptor complexes. In one embodiment of the invention, biological activity of TRAIL is enhanced by employing TRAIL in conjunction with an antibody that is capable of cross-linking TRAIL. Cells that are to be killed may be contacted with both a soluble TRAIL polypeptide and such an antibody.

As one example, cancer or virally infected cells are contacted with an anti-Flag® antibody and a soluble Flag®-TRAIL polypeptide. Preferably, an antibody fragment lacking the Fc region is employed. Bivalent forms of the antibody may bind the Flag® moieties of two soluble Flag®-TRAIL polypeptides that are found in separate dimers or trimers. The antibody may be mixed or incubated with a Flag®-TRAIL polypeptide prior to administration in vivo. When an LZ-TRAIL protein is employed, an antibody directed against the leucine zipper peptide may be substituted for the anti-Flag® antibody, in the foregoing procedures.

Oligomerization is attributable to factors and mechanisms that include, but are not limited to, inter-chain disulfide bonds, and non-covalent interactions such as hydrophobic interactions, as discussed above. Such factors and mechanisms influence the type of oligomers that are formed, which may include higher order oligomers, and may result in protein preparations comprising multiple species of oligomers (e.g., dimers, trimers, hexamers, 12-mers, and so on).

Provided herein are methods for manipulating oligomerization of TRAIL and TRAIL-containing fusion proteins. The products of these methods also are provided.

One approach involves altering the number of cysteine residues in a TRAIL polypeptide or fusion protein. The number of cysteines may be increased or decreased, depending upon whether a corresponding increase or decrease in disulfide bonds is desired.

One may choose to inhibit or promote disulfide bond formation, depending on the form of TRAIL that is desired for a particular purpose. One reason for manipulating disulfide bond formation may be to obtain a more homogeneous protein preparation, by controlling one mechanism of oligomerization. The proportion of oligomers that are of a desired species may be increased through such an approach. Another reason may be to enhance the proportion of a particularly advantageous form of TRAIL in a protein preparation, such as an oligomeric form exhibiting enhanced biological activity.

The amino acid sequence of a TRAIL protein or fusion protein may be altered to increase or decrease the number of cysteine residues. Such sequence alteration may be accomplished by conventional procedures, such as mutagenesis techniques, as discussed above. One alternative for increasing the number of cysteine residues involves adding cysteine-containing peptides, preferably fused to the N-terminus of a TRAIL polypeptide (or included in a fusion protein comprising TRAIL, such as an LZ-TRAIL fusion).

The cysteine residue at position 230 of SEQ ID NO:2 is located within the extracellular domain, which contains the receptor-binding region. One embodiment of the invention is directed to TRAIL polypeptides in which the Cys-230 residue is deleted or substituted. Formation of disulfide bonds involving the Cys-230 residue, including intramolecular disulfides which would occur in the extracellular domain containing the receptor-binding function of the protein, thus is avoided.

Oligomers may be treated with chemical cross-linking reagents. Reagents that stabilize the oligomers, without destroying a desired biological activity, are chosen for use.

Expression Systems

The present invention provides recombinant expression vectors for expression of TRAIL, and host cells transformed with the expression vectors. Any suitable expression system may be employed. The vectors include a DNA encoding a TRAIL polypeptide, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the TRAIL DNA sequence. Thus, a promoter nucleotide sequence is operably linked to an TRAIL DNA sequence if the promoter nucleotide sequence controls the transcription of the TRAIL DNA sequence. An origin of replication that confers the ability to replicate in the desired host cells, and a selection gene by which transformants are identified, are generally incorporated into the expression vector.

In addition, a sequence encoding an appropriate signal peptide can be incorporated into expression vectors. A DNA sequence for a signal peptide (secretory leader) may be fused in frame to the TRAIL sequence so that the TRAIL is initially translated as a fusion protein comprising the signal peptide. A signal peptide that is functional in the intended host cells promotes extracellular secretion of the TRAIL polypeptide. The signal peptide is cleaved from the TRAIL polypeptide upon secretion of TRAIL from the cell.

Suitable host cells for expression of TRAIL polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual,* Elsevier, New York, (1985). Cell-free translation systems could also be employed to produce TRAIL polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium,* and various other species within the genera Pseudomonas, Streptomyces, and Staphylococcus. In a prokaryotic host cell, such as *E. coli,* a TRAIL polypeptide may include an N-terminal methionine residue to facilitate expression of the recombinant polypeptide in the prokaryotic host cell. The N-terminal Met may be cleaved from the expressed recombinant TRAIL polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a TRAIL DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual,* Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

TRAIL alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the TRAIL polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant TRAIL polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CVI/EBNA cell line derived from the African green monkey kidney cell line CVI (ATCC CCL 70) as described by McMahan et al. (*EMBO J.* 10: 2821, 1991).

CHO cells are preferred for use as host cells. One example of a suitable CHO cell line is the cell line designated DX-B11, which is deficient in dihydrofolate reductase (DHFR), as described in Urlaub and Chasin (*Proc. Natl. Acad. Sci USA* 77:4216–4220, 1980), hereby incorporated by reference. DX-B11 cells may be transformed with expression vectors that encode DHFR, which serves as a selectable marker (Kauffman et al., *Meth. in Enzymology*, 185:487–511, 1990). The use of DHFR as a selectable marker, when cells are cultured in medium containing methotrexate, and for amplifying a heterologous DNA inserted into the expression vector, are well known.

In other embodiments, the host cells are CHO cells that can be grown in suspension culture, and that are adapted to grow in media that does not contain serum. The cells may be further adapted to grow in media lacking insulin-like growth factor (IGF-1) and/or transferrin. The host cells may be adapted to grow in media that does not contain any exogenous growth factors that are animal proteins.

Such CHO cell lines may be generated by any suitable procedure. One such procedure is conducted generally as follows. DX-B11 cells are adapted to growth in serum free medium by a gradual reduction of serum supplementation in the media, and replacement of serum with low levels of the growth factors transferrin and insulin-like growth factor (IGF-1), in an enriched cell growth media. Cells adapted to serum-free medium then are weaned off transferrin and insulin-like growth factor-1. The resulting CHO cells maintain vigorous growth and high viability, as well as a DHFR-deficient phenotype, in serum-free, essentially protein-free, media.

Transformed host cells provided herein include, but are not limited to, host cells in which heterologous DNA, including a TRAIL-encoding sequence, is inserted into the cell's genomic DNA. Procedures that result in integration of expression vectors (or portions thereof) into host cell DNA are well known. Conventional procedures may be employed to amplify, or increase the copy number of, heterologous DNA integrated into the genomic DNA of transformed host cells.

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983), for example. A useful system for stable high level expression of mammalian cDNAs in C127 murine mammary epithelial cells can be constructed substantially as described by Cosman et al. (*Mol. Immunol.* 23:935, 1986). A high expression vector, PMLSV N1/N4, described by Cosman et al., *Nature* 312:768, 1984 has been deposited as ATCC 39890. Additional mammalian expression vectors are described in EP-A-0367566, and in WO 91/18982. As one alternative, the vector may be derived from a retrovirus. Additional suitable expression systems are described in the examples below.

One preferred expression system employs Chinese hamster ovary (CHO) cells and an expression vector designated PG5.7. This expression vector is described in U.S. patent application Ser. No. 08/586,509, filed Jan. 11, 1996, and in PCT application publication no. WO 97/25420, which are hereby incorporated by reference. PG5.7 components include a fragment of CHO cell genomic DNA, followed by a CMV-derived promoter, which is followed by a sequence encoding an adenovirus tripartite leader, which in turn is followed by a sequence encoding dihydrofolate reductase (DHFR). These components were inserted into the plasmid vector pGEM1 (Promega, Madison, Wis.). DNA encoding a TRAIL polypeptide (or fusion protein containing TRAIL) may be inserted between the sequences encoding the tripartite leader and DHFR. Methotrexate may be added to the culture medium to increase expression levels, as is recognized in the field.

The fragment of CHO cell genomic DNA in vector PG5.7 enhances expression of TRAIL. A phage lysate containing a fragment of genomic DNA isolated from CHO cells was deposited with the American Type Culture Collection on Jan. 4, 1996, and assigned accession number ATCC 97411. Vector PG5.7 contains nucleotides 8671 through 14507 of the CHO genomic DNA insert in strain deposit ATCC 97411.

A further example of a suitable expression vector is similar to PG5.7, but comprises a multiple cloning site and an internal ribosome binding site (IRES), positioned between the adenovirus tripartite leader and DHFR-encoding sequences. The multiple cloning site comprises several restriction endonuclease recognition sites, at which heterologous DNA (e.g., TRAIL DNA) may be inserted into the vector. The IRES, a 575 bp non-coding region derived from the encephalomyocarditis virus, allows cap-independent internal binding of the ribosome and initiation of translation. For discussion of the use of IRES sequences in expression vectors, including the role such sequences play in allowing dicistronic mRNAs to be translated efficiently, see Kaufman R., Nucleic Acids Research 19:4485, 1991; Oh and Sarnow, *Current Opinion in Genetics and Development* 3:295–300, 1993; and Ramesh et al., *Nucleic Acids Research,* 24:2697–2700, 1996. In addition, the vector may comprise a truncated CHO genomic DNA fragment, shorter than the fragment incorporated into PG5.7, yet still functional in enhancing expression of TRAIL (see WO 97/25420).

For expression of TRAIL, a type II protein lacking a native signal sequence, a heterologous signal sequence or leader functional in mammalian host cells may be added. Examples include the signal sequence for interleukin-7 (IL-7) described in U.S. Pat. No. 4,965,195, the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. Another option is a leader derived from Ig-kappa, such as a leader comprising the amino acid sequence Met-Gly-Thr-Asp-Thr-Leu-Leu-Leu-Trp-Val-Leu-Leu-Leu-Trp-Val-Pro-Gly-Ser-Thr-Gly (SEQ ID NO:25). Further alternatives are cytomegalovirus-derived leaders and signal peptides derived from a growth hormone, as described in more detail below.

A preferred expression system employs a leader sequence derived from cytomegalovirus (CMV). Example 7 illustrates the use of one such leader. In example 7, mammalian host cells were transformed with an expression vector encoding the peptide Met Ala Arg Arg Leu Trp Ile Leu Ser Leu Leu Ala Val Thr Leu Thr Val Ala Leu Ala Ala Pro Ser Gln Lys Ser Lys Arg Arg Thr Ser Ser (SEQ ID NO:9) fused to the N-terminus of an octapeptide designated FLAG® (SEQ ID NO:7, described above), which in turn is fused to the N-terminus of a soluble TRAIL polypeptide. Residues 1 through 29 of SEQ ID NO:9 constitute a CMV-derived leader sequence, whereas residues 30 through 32 are encoded by oligonucleotides employed in constructing the expression vector described in example 7. In one embodiment, DNA encoding a poly-His peptide (e.g., a peptide containing six histidine residues) is positioned between the sequences encoding the CMV leader and the FLAG® peptide.

In another embodiment of the invention, the FLAG® peptide in tie fusion protein described immediately above is replaced with a leucine zipper peptide. Thus, one recombinant expression vector provided herein comprises DNA encoding a fusion protein comprising a CMV leader, a leucine zipper peptide, and a soluble TRAIL polypeptide. One example of such a fusion protein is depicted in FIG. 4 (SEQ ID NO: 13). The protein of FIG. 4 comprises (from N- to C-terminus) a CMV leader (residues 1 through 29 of SEQ ID NO:9); an optional tripeptide Thr-Ser-Ser encoded by oligonucleotides employed in vector construction (residues 30 through 32 of SEQ ID NO:9); a leucine zipper (SEQ ID NO: 15); an optional tripeptide Thr-Arg-Ser encoded by oligonucleotides employed in vector construction, and amino acids 95 to 281 of the human TRAIL protein of SEQ ID NO:2.

Expression systems that employ such CMV-derived leader peptides are useful for expressing proteins other than TRAIL. Expression vectors comprising a DNA sequence that encodes amino acids 1 through 29 of SEQ ID NO:9 are provided herein. In another embodiment, the vector comprises a sequence that encodes amino acids 1 through 28 of SEQ ID NO:9. DNA encoding a desired heterologous protein is positioned downstream of, and in the same reading frame as, DNA encoding the leader. Additional residues (e.g., those encoded by linkers or primers) may be encoded by DNA positioned between the sequences encoding the leader and the desired heterologous protein, as illustrated by the vector described in example 7. As is understood in the pertinent field, the expression vectors comprise promoters and any other desired regulatory sequences, operably linked to the sequences encoding the leader and heterologous protein.

The leader peptide presented in SEQ ID NO:9 may be cleaved after the arginine residue at position 29 to yield the mature secreted form of a protein fused thereto. Alternatively or additionally, cleavage may occur between amino acids 20 and 21, or between amino acids 28 and 29, of SEQ ID NO:9.

The skilled artisan will recognize that the position(s) at which the signal peptide is cleaved may vary according to such factors as the type of host cells employed, whether murine or human TRAIL is expressed by the vector, and the like. Analysis by computer program reveals that the primary cleavage site may be between residues 20 and 21 of SEQ ID NO:9. Cleavage between residues 22 and 23, and between residues 27 and 28, is predicted to be possible, as well. To illustrate, expression and secretion of a soluble murine TRAIL polypeptide resulted in cleavage of a CMV-derived signal peptide at multiple positions. The three most prominent species of secreted protein (in descending order) resulted from cleavage between amino acids 20 and 21 of SEQ ID NO:9, cleavage between amino acids 22 and 23, and cleavage between amino acids 27 and 28.

In one particular expression system, in which the fusion protein of FIG. 4 (SEQ ID NO:13) was expressed in CHO cells, the CMV leader was cleaved at two positions. Two forms of mature protein resulted, one comprising amino acids 21 to 256, and the other comprising amino acids 29 to 256, of SEQ ID NO:13.

A signal peptide comprising amino acids 1 to 20 of the CMV leader of SEQ ID NO:9 is also provided herein. Such a signal peptide may yield a more homogeneous preparation of mature protein, since certain of the above-mentioned alternative signal peptidase cleavage sites are omitted from the leader.

A method for producing a heterologous recombinant protein involves culturing mammalian host cells transformed with such an expression vector under conditions that promote expression and secretion of the heterologous protein, and recovering the protein from the culture medium. Expression systems employing CMV leaders may be used to produce any desired protein, examples of which include, but are not limited to, colony stimulating factors, interferons, interleukins, other cytokines, and cytokine receptors.

A particularly preferred signal peptide for expression of TRAIL polypeptides is a signal peptide derived from a growth hormone gene. One such signal peptide or leader, which is derived from human growth hormone, comprises the following amino acid sequence: Met Ala Thr Gly Ser Arg Thr Ser Leu Leu Leu Ala Phe Gly Leu Leu Cys Leu Pro Trp Leu Gln Glu Gly Ser Ala (SEQ ID NO:19). An example of a DNA sequence that encodes this growth hormone leader is as follows:
ATGGCTACAGGCTCCCGGACGTCCCT-GTCCTGGCTTTTTGGCCTGCTCTGCCT-GCCCTGGCTTCAAGAGGGCAGTGCA (SEQ ID NO:18).

One expression system employing such a signal peptide is described below, in example 14. In alternative embodiments of the invention, CHO cells (described above) are employed as host cells, in place of the CV1-EBNA cells described in example 14. Preferred embodiments of the present invention are directed to expression vectors encoding a fusion protein comprising (from N- to C-terminus) a growth hormone leader, the leucine zipper peptide of SEQ ID NO:15, and a soluble TRAIL polypeptide. In one embodiment, the TRAIL polypeptide is a soluble human TRAIL polypeptide comprising amino acids 95 to 281 of SEQ ID NO:2. Optionally, peptide linkers (which may be encoded by DNA segments resulting from the vector construction technique, for example) are positioned between the growth hormone leader and the leucine zipper, or between the leucine zipper and TRAIL. The leucine zipper moiety promotes oligomerization of the fusion proteins.

One example of such a fusion protein is depicted in FIG. 3. The fusion protein comprises (from N- to C-terminus) a growth hormone-derived leader sequence (SEQ ID NO:19), followed by a tripeptide encoded by an oligonucleotide employed in vector construction (Thr-Ser-Ser), a leucine zipper peptide (SEQ ID NO:15), a tripeptide encoded by an oligonucleotide employed in vector construction (Thr-Arg-Ser), and a soluble human TRAIL polypeptide (amino acids 95 to 281 of SEQ ID NO:2). A DNA sequence encoding the fusion protein, and the amino acid sequence of the fusion protein, are presented in SEQ ID NO:10 and 11, respectively.

Purified TRAIL Protein

The present invention provides purified TRAIL proteins, which may be produced by recombinant expression systems as described above or purified from naturally occurring cells. The desired degree of purity may depend on the intended use of the protein. A relatively high degree of purity is desired when the protein is to be administered in vivo, for example. Advantageously, TRAIL polypeptides are purified such that no protein bands corresponding to other proteins are detectable by SDS-polyacrylamide gel electrophoresis (SDS-PAGE). It will be recognized by one skilled in the pertinent field that multiple bands corresponding to TRAIL protein may be detected by SDS-PAGE, due to differential glycosylation, variations in post-translational processing, and the like, as discussed above. A preparation of TRAIL protein is considered to be purified as long as no bands corresponding to different (non-TRAIL) proteins are visualized. TRAIL most preferably is purified to substantial homogeneity, as indicated by a single protein band upon analysis by SDS-PAGE. The protein band may be visualized by silver staining, Coomassie blue staining, or (if the protein is radiolabeled) by autoradiography.

One process for producing the TRAIL protein comprises culturing a host cell transformed with an expression vector comprising a DNA sequence that encodes TRAIL under conditions such that TRAIL is expressed. The TRAIL protein is then recovered from the culture (from the culture medium or cell extracts). As the skilled artisan will recognize, procedures for purifying the recombinant TRAIL will vary according to such factors as the type of host cells employed and whether or not the TRAIL is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify TRAIL. Some or all of the foregoing purification steps, in various combinations, can be employed to provide a purified TRAIL protein.

In one example of a procedure for producing and purifying TRAIL, Chinese Hamster Ovary (CHO) cells are stably transformed with a recombinant expression vector encoding soluble TRAIL. In one embodiment, the vector encodes a fusion protein comprising a CMV-derived leader, a leucine zipper, and a soluble TRAIL polypeptide, as described in more detail elsewhere herein. The transformed cells are cultured to allow expression and secretion of the soluble LZ-TRAIL protein into the culture supernatant. The culture supernatant then is diluted 5-fold with 20 mM Tris buffer, pH 8.5, and applied to a Q-Sepharose anion exchange column (Pharmacia LKB, Uppsala, Sweden) at a ratio of 1 ml supernatant per 0.3 ml bead volume. The flow-through then is passed over a Fractogel® S-Sepharose cation exhange column (EM Separations, Gibbstown, N.J.) at a ratio of 1/0.06 ml (v/v), washed with five column volumes of buffer, and eluted with a salt gradient of 0 to 1.0M NaCl in 20 mM Tris buffer, pH 8.5. Fractions containing the LZ/TRAIL protein are pooled and dialyzed against Tris Buffered Saline (TBS).

Another example of a protein purification procedure, slightly modified from the procedure described immediately above, is as follows. This procedure may be employed when a leader derived from growth hormone is substituted for the CMV leader, for example. Chinese Hamster Ovary (CHO) cells are stably transformed with a recombinant expression vector encoding GH leader-LZ-TRAIL, and cultured to allow expression and secretion of the soluble LZ-TRAIL protein into the culture supernatant. The culture supernatant then is diluted 5-fold with 25 mM Tris buffer, pH 7.0, and applied to a Q-Sepharose anion exchange column (Pharmacia LKB, Uppsala, Sweden) at a ratio of 1 ml supernatant per 0.3 ml bead volume. The flow-through was concentrated and buffer exchanged into 10 mM Tris, pH 7.0, then passed over a Fractogel® S-Sepharose cation exhange column (EM Separations, Gibbstown, N.J.) at a ratio of 1/0.06 ml (v/v); washed with five column volumes of buffer; and eluted with a 0 to 0.5M NaCl gradient in 10 mM Tris buffer, pH 7.0. Fractions containing the LZ/TRAIL protein were concentrated and applied to an S200 sizing column (Pharmacia) in 10 mM Tris, pH 7.0, 100 mM NaCl, 10% glycerol.

When bacterial host cells are employed, the recombinant protein produced in bacterial culture may be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

When transformed yeast host cells are employed, TRAIL preferably is expressed as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Alternatively, TRAIL polypeptides can be purified by immunoaffinity chromatography. An affinity column containing an antibody that binds TRAIL may be prepared by conventional procedures and employed in purifying TRAIL. Example 4 describes a procedure for generating monoclonal antibodies directed against TRAIL.

Expression of various forms of TRAIL described herein in particular expression systems may yield protein preparations comprising multiple species of oligomers (e.g., dimers, trimers, hexamers, 12-mers, and so on). To illustrate, a mixture of oligomers, including hexamers and trimers, may result from expression of the fusion protein of SEQ ID NO:11 in COS cells. In another illustrative scenario, involving expression of a fusion protein comprising a growth hormone leader, an isoleucine zipper and a spacer-deleted soluble TRAIL polypeptide, 12-mers may be among the resulting oligomers. If a particular species of oligomer is desired for a particular use, that species may be isolated using conventional procedures. An example of a suitable procedure employs size exclusion chromatography.

A TRAIL protein (e.g., a fusion protein or oligomer) prepared using a particular expression system may comprise inter- or intra-molecular disulfide bonds that are disadvantageous for a particular use of the protein. In such a case, the TRAIL protein may be treated with a reducing agent in accordance with conventional techniques. An example of a suitable procedures comprises treating the protein with 5–10 mM DTT (dithiothreitol) for 10 minutes at 37° C. Other suitable reducing agents, such as B-mercaptoethanol (preferably at a concentration of at least 100 mM in the reaction solution), may be substituted for DTT and used in accordance with standard procedures.

To inhibit reoxidation and formation of new disulfide bonds, the protein may be stored in the presence of a reducing agent. One alternative involves further treatment of the protein, after the reducing step, with a sulfhydryl-specific modifying agent. Examples of such agents are iodoacetamide or iodoacetic acid.

Treatment with a reducing agent may be conducted when refolding of a protein into a different conformation is desired. Disulfide bonds, including intramolecular disulfide bonds, are reduced, and the reducing agent then removed to allow refolding of the protein. If promoting disulfide bond formation is desired, oxygen can be bubbled through the reaction solution.

Properties and Uses of TRAIL

Programmed cell death (apoptosis) occurs during embryogenesis, metamorphosis, endocrine-dependent tissue atrophy, normal tissue turnover, and death of immune thymocytes. Regulation of programmed cell death is vital for normal functioning of the immune system. To illustrate, T cells that recognize self-antigens are destroyed through the apoptotic process during maturation of T-cells in the thymus, whereas other T cells are positively selected. The possibility that some T-cells recognizing certain self epitopes (e.g., inefficiently processed and presented antigenic determinants of a given self protein) escape this elimination process and subsequently play a role in autoimmune diseases has been proposed (Gammon et al., *Immunology Today* 12:193, 1991).

Insufficient apoptosis has been implicated in certain conditions, while elevated levels of apoptotic cell death have been associated with other diseases. The desirability of identifying and using agents that regulate apoptosis in treating such disorders is recognized (Kromer, *Advances in Immunology,* 58:211, 1995; Groux et al., *J. Exp. Med.* 175:331, 1992; Sachs and Lotem, *Blood* 82:15, 1993).

Abnormal resistance of T cells toward undergoing apoptosis has been linked to lymphocytosis, lymphadenopathy, splenomegaly, accumulation of self-reactive T cells, autoimmune disease, development of leukemia, and development of lymphoma (Kromer, supra; see especially pages 214–215). Conversely, excessive apoptosis of T cells has been suggested to play a role in lymphopenia, systemic immunodeficiency, and specific immunodeficiency, with specific examples being virus-induced immunodeficient states associated with infectious mononucleosis and cytomegalovirus infection, and tumor-mediated immunosuppression (Kromer, supra; see especially page 214). Depletion of CD4$^+$ T cells in HIV-infected individuals may be attributable to inappropriate activation-induced cell death (AICD) by apoptosis (Groux et al., *J. Exp. Med.* 175:331, 1992).

As demonstrated in examples 5 and 8, TRAIL induces apoptosis of the acute T cell leukemia cell line designated Jurkat clone E6-1. TRAIL thus is a research reagent useful in studies of apoptosis, including the regulation of programmed cell death. Since Jurkat cells are a leukemia cell line arising from T cells, the TRAIL of the present invention finds use in studies of the role TRAIL may play in apoptosis of other transformed T cells, such as other malignant cell types arising from T cells.

TRAIL binds Jurkat cells, as well as inducing apoptosis thereof. TRAIL did not cause death of freshly isolated murine thymocytes, or peripheral blood T cells (PBTs) freshly extracted from a healthy human donor. A number of uses flow from these properties of TRAIL.

TRAIL polypeptides may be used to purify leukemia cells, or any other cell type to which TRAIL binds. Leukemia cells may be isolated from a patient's blood, for example. In one embodiment, the cells are purified by affinity chromatography, using a chromatography matrix having TRAIL bound thereto. The TRAIL attached to the chromatography matrix may be a full length protein, an TRAIL fragment comprising the extracellular domain, an TRAIL-containing fusion protein, or other suitable TRAIL polypeptide described herein. In one embodiment, a soluble TRAIL/Fc fusion protein is bound to a Protein A or Protein G column through interaction of the Fc moiety with the Protein A or Protein G. Alternatively, TRAIL may be used in isolating leukemia cells by flow cytometry.

The thus-purified leukemia cells are expected to die following binding of TRAIL, but the dead cells will still bear cell surface antigens, and may be employed as immunogens in deriving anti-leukemia antibodies. The leukemia cells, or a desired cell surface antigen isolated therefrom, find further use in vaccine development.

Since TRAIL binds and kills leukemia cells (the Jurkat cell line), TRAIL also may be useful in treating leukemia. A therapeutic method involves contacting leukemia cells with an effective amount of TRAIL. In one embodiment, a leukemia patient's blood is contacted ex vivo with an TRAIL polypeptide. The TRAIL may be immobilized on a suitable matrix. TRAIL binds the leukemia cells, thus removing them from the patient's blood before the blood is returned into the patient.

Alternatively or additionally, bone marrow extracted from a leukemia patient may be contacted with an amount of TRAIL effective in inducing death of leukemia cells in the bone marrow. Bone marrow may be aspirated from the sternum or iliac crests, for example, and contacted with TRAIL to purge leukemia cells. The thus-treated marrow is returned to the patient.

TRAIL also binds to, and induces apoptosis of, lymphoma and melanoma cells (see examples 5, 9, and 10). Thus, uses of TRAIL that are analogous to those described above for leukemia cells are applicable to lymphoma and melanoma cells. TRAIL polypeptides may be employed in treating cancer, including, but not limited to, leukemia, lymphoma, and melanoma. In one embodiment, the lymphoma is Burkitt's lymphoma. Table I in example 9 shows that TRAIL had a cytotoxic effect on several Burkitt's lymphoma cell lines. Epstein-Barr virus is an etiologic agent of Burkitt's lymphoma.

TRAIL polypeptides also find use in treating viral infections. Contact with TRAIL caused death of cells infected with cytomegalovirus, but not of the same cell type when uninfected, as described in example 11. The ability of TRAIL to kill cells infected with other viruses can be confirmed using the assay described in example 11. Such viruses include, but are not limited to, encephalomyocarditis virus, Newcastle disease virus, vesicular stomatitis virus, herpes simplex virus, adenovirus-2, bovine viral diarrhea virus, HIV, and Epstein-Barr virus.

An effective amount of TRAIL is administered to a mammal, including a human, afflicted with a viral infection. In one embodiment, TRAIL is employed in conjunction with interferon to treat a viral infection. In the experiment described in example 11, pretreatment of CMV-infected cells with γ-interferon enhanced the level of killing of the infected cells that was mediated by TRAIL. TRAIL may be administered in conjunction with other agents that exert a cytotoxic effect on cancer cells or virus-infected cells.

A wide variety of drugs have been employed in cancer treatment. Examples include, but are not limited to, cisplatin, taxol, etoposide, Novantrone® (mitoxantrone), actinomycin D, camptothecin (or water soluble derivatives thereof), methotrexate, mitomycin (e.g., mitomycin C), dacarbazine (DTIC), and anti-neoplastic antibiotics such as doxorubicin and daunomycin. Drugs employed in cancer therapy may have a cytotoxic or cytostatic effect on cancer cells, or may reduce proliferation of the malignant cells. Cancer treatment may include radiation therapy. In particular embodiments, TRAIL may be co-administered with other proteins in cancer therapy; one such protein is γ-interferon.

Among the texts providing guidance for cancer therapy is *Cancer, Principles and Practice of Oncology*, 4th Edition, DeVita et al., Eds. J. B. Lippincott Co., Philadelphia, Pa. (1993). An appropriate therapeutic approach is chosen according to the particular type of cancer, and other factors such as the general condition of the patient, as is recognized in the pertinent field.

TRAIL may be added to a standard chemotherapy regimen, in treating a cancer patient. For those combinations in which TRAIL and a second anti-cancer agent exert a synergistic effect against cancer cells, the dosage of the second agent may be reduced, compared to the standard dosage of the second agent when administered alone. A method for increasing the sensitivity of cancer cells to TRAIL comprises co-administering TRAIL with an amount of a chemotherapeutic anti-cancer drug that is effective in enhancing sensitivity of cancer cells to TRAIL.

Particular embodiments of the invention are directed to co-administration of TRAIL and methotrexate, etoposide, or mitoxantrone to a cancer patient, including but not limited to prostate cancer patients. One such therapeutic method comprises administration of TRAIL and mitoxantrone (Novantrone®; Immunex Corporation, Seattle, Wash.) to a prostate cancer patient. For descriptions of mitoxantrone or the use thereof in treating prostate cancer, see U.S. Pat. Nos. 4,197,249 and 4,278,689; and Moore et al. (*J. Clinical Oncology* 12:689–694, 1994), which are hereby incorporated by reference. In an in vitro assay in which a prostate tumor cell line was contacted with various concentrations of LZ-TRAIL and Novantrone®, a synergistic effect was seen, in that the combination of LZ-TRAIL and Novantrone® resulting in enhanced tumor cell death. A synergistic effect also was seen when TRAIL and methotrexate were employed in the assay. LZ-TRAIL is a fusion protein comprising a leucine zipper peptide and a soluble TRAIL polypeptide, as described in more detail above and in example 14.

Another embodiment of the invention is directed to contacting colorectal cancer cells (e.g., colon carcinoma cells) with TRAIL and camptothecene. Alternatives include contacting colorectal cancer cells with TRAIL in conjunction with adriamycin (doxorubicin) or mitomycin.

For in vivo use, derivatives of camptothecene that are more water soluble would be advantageous. Examples of such water soluble derivatives are the drugs 7-ethyl-10-[4-(1-piperidino)-1-piperidino]carbonyloxy-camptothecin (CPT-11; irinotecan) and 9-dimethyl-aminomethyl-10-hydroxycamptothecin (topotecan). Camptothecene and the two above-described derivatives are DNA topoisomerase I inhibitors.

A method for treatment of colorectal cancer (e.g., colon carcinoma) comprises administering TRAIL in conjunction with a water soluble derivative of camptothecene, such as irinotecan or topotecan. For further description of the chemical structure of irinotecan and topotecan, or the use thereof in treating cancer, including colorectal cancer, see Rougier et al. (*J. Clinical Oncology*, 15:251–260, January 1997), Pommier (*Seminars in Oncology* Vol. 23, No. 1, Suppl. 3, pp 3–10, February 1996), Lavelle et al. (*Seminars in Oncology* Vol. 23, No. 1, Suppl. 3, pp 11–20, February 1996), Pitot et al. (*J. Clinical Oncology*, 15:2910–2919, August 1997), Kunimoto et al. (*Cancer Research*, 47:5944–5947, Nov. 15, 1987), and Jansen et al. (*Int. J. of Cancer*, 70:335–40, Jan. 27, 1997), all hereby incorporated by reference.

Also provided herein are methods for treating melanoma by administering TRAIL in conjunction with other therapeutic agent(s). In an in vitro assay, actinomycin D and cycloheximide were found to enhance the sensitivity of certain melanoma cell lines to TRAIL. For particular melanoma cell lines that were resistant to TRAIL-mediated cytotoxicity, addition of the protein synthesis inhibitors actinomycin D or cycloheximide rendered the cells more sensitive to TRAIL-induced death. Thus, one method of the present invention comprises co-administering TRAIL, together with actinomycin D or cycloheximide, to a melanoma patient.

Experimental evidence suggests a correlation between the intracellular concentration of an apoptosis inhibitor designated FLIP, and sensitivity of certain tumor cells to TRAIL-mediated cell death. Certain TRAIL-resistant melanoma cell lines expressed relatively high levels of FLIP, whereas lower levels (or undetectable levels) of FLIP were expressed in TRAIL-sensitive melanoma cell lines. Further, addition of actinomycin D to certain TRAIL-resistant melanoma cell lines resulted in a decrease in the intracellular concentration of FLIP. For further discussion of FLIP proteins (FLICE inhibitory proteins) and their involvement in caspase signaling cascades, see Thome et al., (*Nature*, 386:517, 3 April 1997) and Irmler et al. (Nature 388:190, 1997), hereby incorporated by reference.

One approach toward increasing sensitivity of cancer cells (including but not limited to melanoma cells) to TRAIL is inhibiting expression of FLIP in the target cancer cells. Antisense molecules that are derived from a FLIP DNA sequence, and that will inhibit FLIP expression in target cells, may be employed in such an approach.

As used herein, "co-administration" is not limited to simultaneous administration. TRAIL may be administered along with other therapeutic agents, during the course of a treatment regimen. In one embodiment, administration of TRAIL and other therapeutic agents is sequential. An appropriate time course may be chosen by the physician, according to such factors as the nature of a patient's illness, and the patient's condition.

In preferred embodiments of the therapeutic methods described herein, soluble human TRAIL polypeptides, or oligomeric forms thereof, are administered. Oligomers comprising leucine zipper-TRAIL fusion proteins are especially preferred.

In another embodiment, TRAIL is used to kill virally infected cells in cell preparations, tissues, or organs that are to be transplanted. To illustrate, bone marrow may be contacted with TRAIL to kill virus infected cells that may be present therein, before the bone marrow is transplanted into the recipient.

The TRAIL of the present invention may be used in developing treatments for any disorder mediated (directly or indirectly) by defective or insufficient amounts of TRAIL. A therapeutically effective amount of purified TRAIL protein is administered to a patient afflicted with such a disorder. Alternatively, TRAIL DNA sequences may be employed in developing a gene therapy approach to treating such disorders. Disclosure herein of native TRAIL nucleotide sequences permits the detection of defective TRAIL genes, and the replacement thereof with normal TRAIL-encoding genes. Defective genes may be detected in in vitro diagnostic assays, and by comparision of the native TRAIL nucleotide sequence disclosed herein with that of a TRAIL gene derived from a person suspected of harboring a defect in this gene.

The present invention provides pharmaceutical compositions comprising purified TRAIL and a physiologically acceptable carrier, diluent, or excipient. Suitable carriers, diluents, and excipients are nontoxic to recipients at the dosages and concentrations employed. Such compositions may comprise buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients commonly employed in pharmaceutical compositions. Neutral buffered saline or saline mixed with conspecific serum albumin are among the appropriate diluents. The composition may be formulated as a lyophilizate using appropriate excipient solutions (e.g. sucrose) as diluents.

For therapeutic use, purified proteins of the present invention are administered to a patient, preferably a human, for treatment in a manner appropriate to the indication. Thus, for example, the pharmaceutical compositions can be administered locally, by intravenous injection, continuous infusion, sustained release from implants, or other suitable technique. Appropriate dosages and the frequency of administration will depend, of course, on such factors as the nature and severity of the indication being treated, the desired response, the condition of the patient and so forth.

The TRAIL protein employed in the pharmaceutical compositions preferably is purified such that the TRAIL protein is substantially free of other proteins of natural or endogenous origin, desirably containing less than about 1% by mass of protein contaminants residual of production processes. Such compositions, however, can contain other proteins added as stabilizers, carriers, excipients or co-therapeutics.

The TRAIL-encoding DNAs disclosed herein find use in the production of TRAIL polypeptides, as discussed above. Fragments of the TRAIL nucleotide sequences are also useful. In one embodiment, such fragments comprise at least about 17 consecutive nucleotides, more preferably at least 30 consecutive nucleotides, of the human or murine TRAIL DNA disclosed herein. DNA and RNA complements of said fragments are provided herein, along with both single-stranded and double-stranded forms of the TRAIL DNA of SEQ ID NOS:1, 3 and 5.

Among the uses of such TRAIL nucleic acid fragments are use as a probe or as primers in a polymerase chain reaction (PCR). As one example, a probe corresponding to the extracellular domain of TRAIL may be employed. The probes find use in detecting the presence of TRAIL nucleic acids in in vitro assays and in such procedures as Northern and Southern blots. Cell types expressing TRAIL can be identified as well. Such procedures are well known, and the skilled artisan can choose a probe of suitable length, depending on the particular intended application. For PCR, 5' and 3' primers corresponding to the termini of a desired TRAIL DNA sequence are employed to isolate and amplify that sequence, using conventional techniques.

Other useful fragments of the TRAIL nucleic acids are antisense or sense oligonucleotides comprising a single-stranded nucleic acid sequence (either RNA or DNA) capable of binding to target TRAIL MRNA (sense) or TRAIL DNA (antisense) sequences. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of TRAIL proteins.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as,poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application WO 90/13641). Alternatively, other promotor sequences may be used to express the oligonucleotide.

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antibodies Immunoreactive with TRAIL

The TRAIL proteins of the present invention, or immunogenic fragments thereof, may be employed in generating antibodies. The present invention thus provides antibodies that specifically bind TRAIL, i.e., the antibodies bind to TRAIL via the antigen-binding sites of the antibody (as opposed to non-specific binding).

Polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988). Production of monoclonal antibodies that are immunoreactive with TRAIL is further illustrated in example 4 below.

Antigen-binding fragments of such antibodies, which may be produced by conventional techniques, are also encompassed by the present invention. Examples of such fragments include, but are not limited to, Fab, F(ab'), and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

Among the uses of the antibodies is use in assays to detect the presence of TRAIL polypeptides, either in vitro or in vivo. The antibodies find further use in purifying TRAIL by affinity chromatography.

Those antibodies that additionally can block binding of TRAIL to target cells may be used to inhibit a biological activity of TRAIL. A therapeutic method involves in vivo administration of such an antibody in an amount effective in inhibiting a TRAIL-mediated biological activity. Disorders mediated or exacerbated by TRAIL, directly or indirectly, are thus treated. Monoclonal antibodies are generally preferred for use in such therapeutic methods.

Antibodies directed against TRAIL may be useful for treating thrombotic microangiopathies. One such disorder is thrombotic thrombocytopenic purpura (TTP) (Kwaan, H. C., *Semin. Hematol.,* 24:71, 1987; Thompson et al., *Blood,* 80:1890, 1992). Increasing TTP-associated mortality rates have been reported by the U.S. Centers for Disease Control (Torok et al., *Am. J. Hematol.* 50:84, 1995).

Plasma from patients afflicted with TTP (including HIV$^+$ and HIV$^-$ patients) induces apoptosis of human endothelial cells of dermal microvascular origin, but not large vessel origin (Laurence et al., *Blood,* 87:3245, Apr. 15, 1996). Plasma of TTP patients thus is thought to contain one or more factors that directly or indirectly induce apoptosis. In the assay described in example 13 below, polyclonal antibodies raised against TRAIL inhibited TTP plasma-induced apoptosis of dermal microvascular endothelial cells. The data presented in example 13 suggest that TRAIL is present in the serum of TTP patients, and may play a role in inducing apoptosis of microvascular endothelial cells.

Another thrombotic microangiopathy is hemolytic-uremic syndrome (HUS) (Moake, J. L., Lancet, 343:393, 1994; Melnyk et al., (Arch. Intern. Med., 155:2077, 1995; Thompson et al., supra). One embodiment of the invention is directed to use of an anti-TRAIL antibody to treat the condition that is often referred to as "adult HUS" (even though it can strike children as well). A disorder known as childhood/diarrhea-associated HUS differs in etiology from adult HUS.

Other conditions characterized by clotting of small blood vessels may be treated using anti-TRAIL antibodies. Such conditions include but are not limited to the following. Cardiac problems seen in about 5–10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated.

In one embodiment, a patient's blood or plasma is contacted with an anti-TRAIL antibody ex vivo. The antibody (preferably a monoclonal antibody) may be bound to a suitable chromatography matrix by conventional procedures. The patient's blood or plasma flows through a chromatography column containing the antibody bound to the matrix, before being returned to the patient. The immobilized antibody binds TRAIL, thus removing TRAIL protein from the patient's blood.

In an alternative embodiment, the antibodies are administered in vivo, in which case blocking antibodies are desirably employed. Such antibodies may be identified using any suitable assay procedure, such as by testing antibodies for the ability to inhibit binding of TRAIL to target cells. Alternatively, blocking antibodies may be identified in assays for the ability to inhibit a biological effect of the binding of TRAIL to target cells. Example 12 illustrates one suitable method of identifying blocking antibodies, wherein antibodies are assayed for the ability to inhibit TRAIL-mediated lysis of Jurkat cells.

The present invention thus provides a method for treating a thrombotic microangiopathy, involving use of an effective amount of an antibody directed against TRAIL. Antibodies of the present invention may be employed in in vivo or ex vivo procedures, to inhibit TRAIL-mediated damage to (e.g., apoptosis of) microvascular endothelial cells.

Anti-TRAIL antibodies may be employed in conjunction with other agents useful in treating a particular disorder. In an in vitro study reported by Laurence et al. (Blood 87:3245, 1996), some reduction of TTP plasma-mediated apoptosis of microvascular endothelial cells was achieved by using an anti-Fas blocking antibody, aurintricarboxylic acid, or normal plasma depleted of cryoprecipitate.

Thus, a patient may be treated with an agent that inhibits Fas-ligand-mediated apoptosis of endothelial cells, in combination with an agent that inhibits TRAIL-mediated apoptosis of endothelial cells. In one embodiment, an anti-TRAIL blocking antibody and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in PCT application publication number WO 95/10540, hereby incorporated by reference.

Pharmaceutical compositions comprising an antibody that is immunoreactive with TRAIL, and a suitable, diluent, excipient, or carrier, are provided herein. Suitable components of such compositions are as described above for the compositions containing TRAIL proteins.

The following examples are provided to illustrate particular embodiments of the present invention, and are not to be construed as limiting the scope of the invention.

EXAMPLE 1

Isolation of a Human TRAIL DNA

DNA encoding a human TRAIL protein of the present invention was isolated by the following procedure. A TBLASTN search of the dbEST data base at the National Center for Biological Information (NCBI) was performed, using the query sequence LVVXXXGLYYVYXQVXF (SEQ ID NO:8). This sequence is based upon the most conserved region of the TNF ligand family (Smith et al., Cell, 73:1349, 1993). An expressed sequence tag (EST) file, GenBank accession number Z36726, was identified using these search parameters. The GenBank file indicated that this EST was obtained from a human heart atrium cDNA library.

Two 30-bp oligonucleotides based upon sequences from the 3' and 5' ends of this EST file were synthesized. The oligonucleotide from the 3' end had the sequence TGAAATCGAAAGTATGTTTGGGAATAGATG (complement of nucleotides 636 to 665 of SEQ ID NO:1) and the 5' oligonucleotide was TGACGAAGAGAGTAT-GAACAGCCCCTGCTG (nucleotides 291 to 320 of SEQ ID NO:1). The oligonucleotides were 5' end labeled with $^{32}$P γ-ATP and polynucleotide kinase. Two λgt10 cDNA libraries were screened by conventional methods with an equimolar mixture of these labeled oligonucleotides as probe. One library was a human heart 5' stretch cDNA library (Stratagene Cloning Systems, La Jolla, Calif.). The other was a peripheral blood lymphocyte (PBL) library prepared as follows: PBLs were obtained from normal human volunteers and treated with 10 ng/ml of OKT3 (an anti-CD3 antibody) and 10 ng/ml of human IL-2 for six days. The PBL cells were washed and stimulated with 500 ng/ml of ionomycin (Calbiochem) and 10 ng/ml PMA for 4 hours. Messenger RNA was isolated from the stimulated PBL cells. cDNA synthesized on the mRNA template was packaged into λgt10 phage vectors (Gigapak®, Stratagene Cloning Systems, La Jolla, Calif.).

Recombinant phages were plated onto E. coli strain C600-HFL and screened using standard plaque hybridization techniques. Nitrocellulose filters were lifted from these plates in duplicate, and hybridized with the $^{32}$P-labeled oligonucleotides overnight at 67° C. in a solution of 60 mM Tris pH 8.0, 2 mM EDTA, 5×Denhardt's Solution, 6×SSC, 1 mg/ml n-lauroyl sarcosine, 0.5% NP40, and 4 µg/ml SS salmon sperm DNA. The filters were then washed in 3×SSC at 67° C. for thirty minutes.

From the heart 5' stretch cDNA library, one positive plaque was obtained out of approximately one million plaques. This clone did not include the 3' end of the gene. Using the PBL library, approximately 50 positive plaques were obtained out of 500,000 plaques. Fifteen of these first round positive plaques were picked, and the inserts from the enriched pools were amplified using oligonucleotide primers designed to amplify phage inserts. The resulting products were resolved by 1.5% agarose gel electrophoresis, blotted onto nitrocellulose, and analyzed by standard Southern blot technique using the $^{32}$P-labeled 30-mer oligonucleotides as probes. The two plaque picks that produced the largest bands by Southern analysis were purified by secondary screening, and isolated phage plaques were obtained using the same procedures described above.

DNA from the isolated phages was prepared by the plate lysis method, and the cDNA inserts were excised with EcoRI, purified by electrophoresis using 1.5% agarose in Tris-Borate-EDTA buffer, and ligated into the pBluescript® SK(+) plasmid. These inserts were then sequenced by conventional methods, and the resulting sequences were aligned.

The nucleotide sequence of a human TRAIL DNA is presented in SEQ ID NO:1 and the amino acid sequence encoded thereby is presented in SEQ ID NO:2. This human TRAIL protein comprises an N-terminal cytoplasmic domain (amino acids 1–18), a transmembrane region (amino acids 19–38), and an extracellular domain (amino acids 39–281). The calculated molecular weight of this protein is 32,508 daltons.

E. coli strain DH10B cells transformed with a recombinant vector containing this TRAIL DNA were deposited with the American Type Culture Collection on Jun. 14, 1995, and assigned accession no. 69849. The deposit was made under the terms of the Budapest Treaty. The recombinant vector in the deposited strain is the expression vector pDC409 (described in example 5). The vector was digested with SalI and NotI, and human TRAIL DNA that includes the entire coding region shown in SEQ ID NO:1 was ligated into the digested vector.

EXAMPLE 2
Isolation of DNA Encoding a Truncated TRAIL

DNA encoding a second human TRAIL protein was isolated as follows. This truncated TRAIL does not exhibit the ability to induce apoptosis of Jurkat cells.

PCR analysis, using the 30-mers described in example 1 as the 5' and 3' primers, indicated that 3 out of 14 of the first round plaque picks in example 1 contained shorter forms of the TRAIL DNA. One of the shortened forms of the gene was isolated, ligated into the pBluescript® SK(+) cloning vector (Stratagene Cloning Systems, La Jolla, Calif.) and sequenced.

The nucleotide sequence of this DNA is presented in SEQ ID NO:3. The amino acid sequence encoded thereby is presented in SEQ ID NO:4. The encoded protein comprises an N-terminal cytoplasmic domain (amino acids 1–18), a transmembrane region (amino acids 19–38), and an extracellular domain (amino acids 39–101).

The DNA of SEQ ID NO:3 lacks nucleotides 359 through 506 of the DNA of SEQ ID NO:1, and is thus designated the human TRAIL deletion variant (huTRAILdv) clone. The deletion causes a shift in the reading frame, which results in an in-frame stop codon after amino acid 101 of SEQ ID NO:4. The DNA of SEQ ID NO:3 thus encodes a truncated protein. Amino acids 1 through 90 of SEQ ID NO:2 are identical to amino acids 1 through 90 of SEQ ID NO:4. However, due to the deletion, the C-terminal portion of the huTRAILdv protein (amino acids 91 through 101 of SEQ ID NO:4) differs from the residues in the corresponding positions in SEQ ID NO:2.

The huTRAILdv protein lacks the above-described conserved regions found at the C-terminus of members of the TNF family of proteins. The inability of this huTRAILdv protein to cause apoptotic death of Jurkat cells further confirms the importance of these conserved regions for biological activity.

EXAMPLE 3
DNA Encoding a Murine TRAIL

DNA encoding a murine TRAIL was isolated by the following procedure. A cDNA library comprising cDNA derived from the mouse T cell line 7B9 in the vector λZAP was prepared as described in Mosley et al. (*Cell* 59:335, 1989). DNA from the library was transferred onto nitrocellulose filters by conventional techniques.

Human TRAIL DNA probes were used to identify hybridizing mouse cDNAs on the filters. Two separate probes were used, in two rounds of screening. PCR reaction products about 400 bp in length, isolated and amplified using the human TRAIL DNA as template, were employed as the probe in the first round of screening. These PCR products consisted of a fragment of the human TRAIL coding region. The probe used in the second round of screening consisted of the entire coding region of the human TRAIL DNA of SEQ ID NO:1. A random primed DNA labeling kit (Stratagene, La Jolla, Calif.) was used to radiolabel the probes.

Hybridization was conducted at 37° C. in 50% formamide, followed by washing with 1×SSC, 0.1% SDS at 50° C. A mouse cDNA that was positive in both rounds of screening was isolated.

The nucleotide sequence of this DNA is presented in SEQ ID NO:5 and the amino acid sequence encoded thereby is presented in SEQ ID NO:6. The encoded protein comprises an N-terminal cytoplasmic domain (amino acids 1–17), a transmembrane region (amino acids 18–38), and an extracellular domain (amino acids 39–291). This mouse TRAIL is 64% identical to the human TRAIL of SEQ ID NO:2, at the amino acid level. The coding region of the mouse TRAIL nucleotide sequence is 75% identical to the coding region of the human nucleotide sequence of SEQ ID NO:1.

EXAMPLE 4
Antibodies that Bind TRAIL

This example illustrates the preparation of monoclonal antibodies that specifically bind TRAIL. Suitable immunogens that may be employed in generating such antibodies include, but are not limited to, purified TRAIL protein or an immunogenic fragment thereof (e.g., the extracellular domain), fusion proteins containing TRAIL polypeptides (e.g., soluble TRAIL/Fc fusion proteins), and cells expressing recombinant TRAIL on the cell surface.

Known techniques for producing monoclonal antibodies include those described in U.S. Pat. No. 4,411,993. Briefly, mice are immunized with TRAIL as an immunogen emulsified in complete Freund's adjuvant, and injected in amounts ranging from 10–100 µg subcutaneously or intraperitoneally. Ten to twelve days later, the immunized animals are boosted with additional TRAIL emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immuno-sorbent Assay) for TRAIL antibodies.

Following detection of an appropriate antibody titer, positive animals are provided one last intravenous injection of TRAIL in saline. Three to four days later, the animals are sacrificed, spleen cells harvested, and spleen cells are fused to a murine myeloma cell line such as NS1 or, preferably, P3x63Ag 8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified TRAIL by adaptations of the techniques disclosed in Engvall et al. (*Immunochem.* 8:871, 1971) and in U.S. Pat. No. 4,703,004. Positive hybridoma cells can be injected intraperitoneally into syngeneic BALB/c mice to produce ascites containing high concentrations of anti-TRAIL monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can be used, as can affinity chromatography based upon binding to TRAIL.

EXAMPLE 5
DNA Laddering Apoptosis Assay

Human TRAIL was expressed and tested for the ability to induce apoptosis. Oligonucleotides were synthesized that corresponded to the 3' and 5' ends of the coding region of the human TRAIL gene, with SalI and NotI restriction sites incorporated at the ends of the oligonucleotides. The coding region of the human TRAIL gene was amplified by standard PCR techniques, using these oligonucleotides as primers. The PCR reaction products were digested with the restriction endonucleases SalI and NotI, then inserted into SalI/NotI-digested vector pDC409. pDC409 is an expression vector for use in mammalian cells, but is also replicable in E. coli cells.

pDC409 is derived from an expression vector designated pDC406 (described in McMahan et al., *EMBO J.* 10:2821, 1991, and in PCT application WO 91/18982, hereby incorporated by reference). pDC406 contains origins of replication derived from SV40, Epstein-Barr virus and pBR322 and is a derivative of HAV-EO described by Dower et al., *J. Immunol.* 142:4314 (1989). pDC406 differs from HAV-EO by the deletion of an intron present in the adenovirus 2 tripartite leader sequence in HAV-EO. DNA inserted into a multiple cloning site (containing a number of restriction endonuclease cleavage sites) is transcribed and translated using regulatory elements derived from HIV and adenovirus. The vector also contains a gene that confers ampicillin resistance.

pDC409 differs from pDC406 in that a Bgl II site outside the mcs has been deleted so that the mcs Bgl II site is unique. Two Pme 1 sites and one Srf 1 site have been added to the mcs, and three stop codons (TAG) have been positioned downstream of the mcs to function in all three reading frames. A T7 primer/promoter has been added to aid in the DNA sequencing process.

The monkey kidney cell line CV-1/EBNA-1 (ATCC CRL 10478) was derived by transfection of the CV-1 cell line (ATCC CCL 70) with a gene encoding Epstein-Barr virus nuclear antigen-1 (EBNA-1) that constitutively expresses EBNA-1 driven from the human CMV intermediate-early enhancer/promoter, as described by McMahan et al., supra. The EBNA-1 gene allows for episomal replication of expression vectors, such as pDC409, that contain the EBV origin of replication.

CV1/EBNA cells grown in Falcon T175 flasks were transfected with 15 µg of either "empty" pDC409 or pDC409 containing the human TRAIL coding region. The transformed cells were cultured for three days at 37° C. and 10% $CO_2$. The cells then were washed with PBS, incubated for 20 minutes at 37° C. in 50 mM EDTA, scraped off of the flask with a cells scraper, and washed once in PBS. Next, the cells were fixed in 1% paraformaldehyde PBS for 10 minutes at 4° C., and washed 3× in PBS.

Jurkat cells were used as the target cells in this assay, to determine whether the TRAIL-expressing cells could induce apoptosis thereof. The Jurkat cell line, clone E6-1, is a human acute T cell leukemia cell line available from the American Type Culture Collection under accession no. ATCC TIB 152, and described in Weiss et al. (*J. Immunol.* 133:123–128, 1984). The Jurkat cells were cultured in RPMI media supplemented with 10% fetal bovine serum and 10 µg/ml streptomycin and penicillin to a density of 200,000 to 500,000 cells per ml. Four million of these cells per well were co-cultured in a 6 well plate with 2.5 mls of media with various combinations of fixed cells, supernatants from cells transfected with Fas ligand, and various antibodies, as indicated below.

After four hours the cells were washed once in PBS and pelleted at 1200 RPM for 5 minutes in a desktop centrifuge. The pellets were resuspended and incubated for ten minutes at 4° C. in 500 µl of buffer consisting of 10 mM Tris-HCl, 10 mM EDTA, pH 7.5, and 0.2% Triton X-100, which lyses the cells but leaves the nuclei intact. The lysate was then spun at 4° C. for ten minutes in a micro-centrifuge at 14,000 RPM. The supernatants were removed and extracted three times with 1 ml of 25:24:1 phenol-chloroform-isoamyl alcohol, followed by precipitation with NaOAC and ethanol in the presence of 1 µg of glycogen carrier (Sigma).

The resulting pellets were resuspended in 10 mM Tris-HCl, 10 mM EDTA, pH 7.5, and incubated with 10 µg/ml RNase A at 37° C. for 20 minutes. The DNA solutions were then resolved by 1.5% agarose gel electrophoresis in Tris-Borate EDTA buffer, stained with ethidium bromide and photographed while trans-illuminated with UV light.

The results were as follows. Fixed CV1/EBNA cells transfected with either pDC409 or pDC409-TRAIL produced no detectable DNA laddering. pDC409-TRAIL fixed cells co-cultured with Jurkat cells produced DNA laddering, but pDC409 fixed cells co-cultured with Jurkat cells did not.

DNA laddering was also seen when Jurkat cells were co-cultured with concentrated supernatants from COS cells transfected with DNA encoding human Fas ligand in pDC409. The supernatants are believed to contain soluble Fas ligand that is proteolytically released from the cell surface. The Fas ligand-induced DNA laddering could be blocked by adding 10 µg/ml of a soluble blocking monoclonal antibody directed against Fas. This same antibody could not inhibit laddering of Jurkat DNA by the pDC409-TRAIL cells, which indicates that TRAIL does not induce apoptosis through Fas.

In the same assay procedure, fixed CV1/EBNA cells transfected with pDC409-TRAIL induced DNA laddering in U937 cells. U937 (ATCC CRL 1593) is a human histiocytic lymphoma cell line. The ratio of effector to target cells was 1:4 (the same as in the assay on Jurkat target cells).

The fragmentation of cellular DNA into a pattern known as DNA laddering is a hallmark of apoptosis. In the foregoing assay, TRAIL induced apoptosis of a leukemia cell line and a lymphoma cell line.

EXAMPLE 6
Northern Blot Analysis

Expression of TRAIL in a number of different tissue types was analysed in a conventional northern blot procedure. Northern blots containing poly $A^{30}$ RNA from a variety of adult human tissues (multiple tissue northern blots I and II) were obtained from Clonetech (Palo Alto, Calif.). Other blots were prepared by resolving RNA samples on a 1.1% agarose-formaldehyde gel, blotting onto Hybond-N as recommended by the manufacturer (Amersham Corporation), and staining with methylene blue to monitor RNA concentrations. The blots were probed with an antisense RNA riboprobe corresponding to the entire coding region of human TRAIL.

Human TRAIL mRNA was detected in peripheral blood lymphocytes, colon, small intestine, ovary, prostate, thymus, spleen, placenta, lung, kidney, heart, pancreas, and skeletal muscle. TRAIL transcripts were found to be abundant in the large cell anaplastic lymphoma cell line Karpas 299 (Fischer et al., *Blood*, 72:234, 1988) and in tonsilar T cells. TRAIL message was present to a lesser degree in the Burkitt lymphoma cell line designated Raji.

TRAIL mRNA was not detected in testis, brain, or liver, or in several T cell lines. Little or no TRAIL transcripts were detected in freshly isolated peripheral blood T cells (PBT), either unstimulated or stimulated with PMA and calcium ionophore for 20 hours.

EXAMPLE 7

Production of a Soluble TRAIL Polypeptide

A soluble human TRAIL polypeptide comprising amino acids 95 to 281 of SEQ ID NO:2 was prepared as follows. This polypeptide is a fragment of the extracellular domain, lacking the spacer region discussed above.

An expression vector encoding soluble human TRAIL was constructed by fusing in-frame DNA encoding the following amino acid sequences (listed from N- to C-terminus): a leader sequence derived from human cytomegalovirus (CMV), a synthetic epitope designated Flag®, and amino acids 95–281 of human TRAIL. The Flag® octapeptide (SEQ ID NO:7) facilitates purification of proteins fused thereto, as described above and in Hopp et al. (*Biotechnology* 6:1204–1210, 1988).

The TRAIL-encoding DNA fragment was isolated and amplified by polymerase chain reaction (PCR), using oligonucleotide primers that defined the termini of a DNA fragment encoding amino acids 95–281 of SEQ ID NO:2. The 3' primer was a 31-mer that additionally added a NotI site downstream of the TRAIL-encoding sequence. The 5' primer added an SpeI site and a Flag® epitope encoding sequence upstream of the TRAIL-encoding sequence. PCR was conducted by conventional procedures, using the above-described human TRAIL cDNA as the template.

The reaction products were digested with SpeI and NotI, and inserted into the expression vector pDC409 (described in example 5), which had been cleaved with SalI and NotI. Annealed oligonucleotides that form a SalI-SpeI fragment encoding a CMV open reading frame leader were also ligated into the vector. The amino acid sequence of the CMV-derived leader is presented as SEQ ID NO:9. Amino acids 1 to 29 of SEQ ID NO:9 are encoded by CMV DNA, whereas amino acids 30 to 32 are encoded by oligonucleotides employed in constructing the vector. *E. coli* cells were transfected with the ligation mixture, and the desired recombinant expression vector was isolated therefrom.

CV1-EBNA cells (ATCC CRL 10478; described in example 5) were transfected with the recombinant vector, which is designated pDC409-Flag-shTRAIL, and cultured to allow expression and secretion of the soluble Flag®-TRAIL polypeptide. Culture supernatants were harvested 3 days after transfection and applied to a column containing an anti-Flag® antibody designated M2 immobilized on a solid support. The column then was washed with PBS. The monoclonal antibody M2 is described in Hopp et al., supra, and available from Kodak Scientific Imaging Systems, New Haven, Conn. 800 µl fractions were eluted from the column with 50 mM citrate, and immediately neutralized in 0.45 ml 1 M Tris (pH 8). Fractions were adjusted to 10% glycerol and stored at −20° C. until needed.

This soluble recombinant Flag®/human TRAIL expressed in CV1/EBNA cells has an apparent molecular weight of 28 kD when analyzed by SDS-polyacrylamide gel electrophoresis (SDS-PAGE). The Flag® moiety contributes an estimated 880 daltons to the total molecular weight. Gel filtration analysis of purified soluble Flag®/TRAIL suggests that the molecule is multimeric in solution with a size of ~80 kD. While not wishing to be bound by theory, the gel filtration analysis suggests that the soluble recombinant Flag®/human TRAIL naturally formed a combination of dimers and trimers, with trimers predominating.

An expression vector designated pDC409-Flag-smTRAIL, which encodes a CMV leader-Flag®-soluble murine TRAIL protein, was constructed by analogous procedures. A DNA fragment encoding a soluble murine TRAIL polypeptide was isolated and amplified by PCR. Oligonucleotides that defined the termini of DNA encoding amino acids 99 to 291 of the murine TRAIL sequence of SEQ ID NO:6 were employed as the 5' and 3' primers in the PCR.

EXAMPLE 8

Lysis of Leukemia Cells by Soluble TRAIL

In example 5, cells expressing human TRAIL induced apoptosis of Jurkat cells (a leukemia cell line). In the following study, a soluble human TRAIL polypeptide killed Jurkat cells.

Jurkat cells were cultured to a density of 200,000 to 500,000 cells per ml in RPMI medium supplemented with 10% fetal bovine serum, 100 µg/ml streptomycin, and 100 µg/ml penicillin. The cells (in 96-well plates at 50,000 cells per well in a volume of 100 µl) were incubated for twenty hours with the reagents indicated in FIG. 1. "TRAIL supe." refers to conditioned supernatant (10 µl per well) from CV1/EBNA cells transfected with pDC409-Flag-shTRAIL (see example 7). "Control supe." refers to supernatant from CV1/EBNA cells transfected with empty vector. Where indicated, immobilized anti-Flag® antibody M2 ("Imm. M2") was added at a concentration of 10 µg/ml in a volume of 100 µl per well and allowed to adhere either overnight at 4° C. or for 2 hours at 37° C., after which wells were aspirated and washed twice with PBS to remove unbound antibody. Jurkat cells treated with Fas ligand or M3, a blocking monoclonal antibody directed against Fas, (Alderson et al., *J. Exp. Med.* 181:71, 1995; and PCT application WO 95/10540) were included in the assay as indicated.

Metabolic activity of the thus-treated cells was assayed by metabolic conversion of alamar Blue dye, in the following procedure. Alamar Blue conversion was measured by adding 10 µl of alamar Blue dye (Biosource International, Camarillo, Calif.) per well, and subtracting the optical density (OD) at 550–600 nm at the time the dye was added from the OD 550–600 nm after four hours. No conversion of dye is plotted as 0 percent viability, and the level of dye conversion in the absence of TRAIL is plotted as 100 percent viability. Percent viability was calculated by multiplying the ratio of staining of experimental versus control cultures by 100.

The results are presented in FIG. 1. Error bars represent the standard deviation of measurements from four independent wells, and the values are the average of these measurements.

The TRAIL-containing supernatant caused a significant reduction in viability of Jurkat cells. A greater reduction of cell viability resulted from contact with a combination of TRAIL-containing supernatant and immobilized anti-Flag® antibody M2. One possible explanation is that M2 facilitates cross-linking of the Flag®/TRAIL-receptor complexes, thereby increasing the strength of signaling.

Fas ligand demonstrated the ability to kill Jurkat cells. The anti-Fas antibody M3 inhibited the activity of Fas ligand, but not the activity of TRAIL.

In order to confirm that the changes in dye conversion in the alamar Blue assay were due to cell death, the decrease in cell viability induced by TRAIL was confirmed by staining the cells with trypan blue.

EXAMPLE 9
Lysis of Leukemia and Lymphoma Cells

In examples 5 and 8, TRAIL induced apoptosis of a leukemia cell line (Jurkat) and a lymphoma cell line (U937). The following study further demonstrates the ability of TRAIL to kill leukemia and lymphoma cells.

The human cell lines indicated in Table I were cultured to a density of 200,000 to 500,000 cells per ml in RPMI medium supplemented with 10% fetal bovine serum, 100 µg/ml streptomycin, and 100 µg/ml penicillin. The cells (in 96-well plates at 50,000 cells per well in a volume of 100 µl) were incubated for twenty hours with conditioned supernatants (10 µl per well) from pDC409-Flag-shTRAIL transfected CV1/EBNA cells.

Metabolic activity was assayed by conversion of alamar Blue dye, in the assay procedure described in example 8. The results are presented in Table I.

In order to confirm that the changes in dye conversion in the alamar Blue assay were due to cell death, the decrease in cell viability induced by TRAIL was confirmed by staining the cells with trypan blue. Crystal violet staining, performed as described by Flick and Gifford (*J. Immunol. Methods* 68:167–175, 1984), also confirmed the results seen in the alamar Blue assay. The apoptotic nature of the cell death was confirmed by trypan blue staining and visualization of apoptotic fragmentation by microscopy.

As shown in Table I, many cancer cell lines were sensitive to TRAIL mediated killing. The susceptibility of additional cell types to TRAIL mediated apoptosis can be determined using the assay procedures described in this examples section.

TRAIL exhibited no significant cytotoxic effect on the cell lines THP-1 K562, Karpas 299, and MP-1. K299, also known as Karpas 299, (DSM-ACC31) was established from peripheral blood of a male diagnosed with high grade large cell anaplastic lymphoma (Fischer et al., *Blood*, 72:234, 1988). MP-1 is a spontaneously derived EBV-transformed B cell line (Goodwin et al., *Cell* 73:447, 1993). While not wishing to be bound by theory, it is possible that these four cell lines do not express a receptor for TRAIL, or are characterized by upregulation of a gene that inhibits apoptosis.

TABLE 1

Effect of soluble TRAIL on cell line viability

| Cell Line | Description | Percent Viability[a] |
|---|---|---|
| Bjab | Burkitt lymphoma | 0.5 ± 3.8 |
| Ramos | Burkitt lymphoma | 12.1 ± 2.1 |
| U937 | histiocytic lymphoma | 25.2 ± 8.2 |
| HL60 | promyelocytic leukemia | 59.5 ± 3.2 |
| Raji | Burkitt lymphoma | 64.9 ± 4.5 |
| Daudi | Burkitt lymphoma | 70.2 ± 4.2 |
| THP-1 | monocytic cell line | 92.3 ± 6.8 |
| K562 | chronic myelogenous leukemia | 97.1 ± 4.8 |
| K 299 | large cell anaplastic lymphoma | 99.0 ± 4.3 |
| MP-1 | spontaneous B cell line | 104.9 ± 11.7 |

[a]Results are means ± SEMs of 4 wells for each data point

EXAMPLE 10
Cross-Species Activity of TRAIL

Interspecies cross-reactivity of human and murine TRAIL was tested as follows. Murine and human TRAIL were incubated with the human melanoma cell line A375 (ATCC CRL 1619). Since this is an adherent cell line, a crystal violet assay, rather than alamar Blue, was used to determine cell viability. A375 cells were cultured in DMEM supplemented with 10% fetal bovine serum, 100 µg/ml streptomycin, and 100 µg/ml penicillin. The cells (in 96-well plates at 10,000 cells per well in a volume of 100 µl) were incubated for 72 hours with the soluble murine TRAIL described in example 7. Crystal violet staining was performed as described by (Flick and Gifford (*J. Immunol. Methods* 68:167–175, 1984). The results demonstrated that both human and murine TRAIL are active on these human cells, in that murine and human TRAIL killed A375 cells.

The ability of human TRAIL to act on murine cells was tested, using the immortalized murine fibroblast cell line L929. Incubation of L929 cells with either human or murine TRAIL resulted in a decrease in crystal violet staining, thus demonstrating that human and murine TRAIL are active on (induced apoptosis of) murine cells. In addition to crystal violet, cell death was confirmed by trypan-blue staining.

EXAMPLE 11
Lysis of CMV-Infected Cells

The following experiment demonstrates that the soluble Flag®-human TRAIL protein prepared in example 7 has a cytotoxic effect on virally infected cells.

Figure 2:
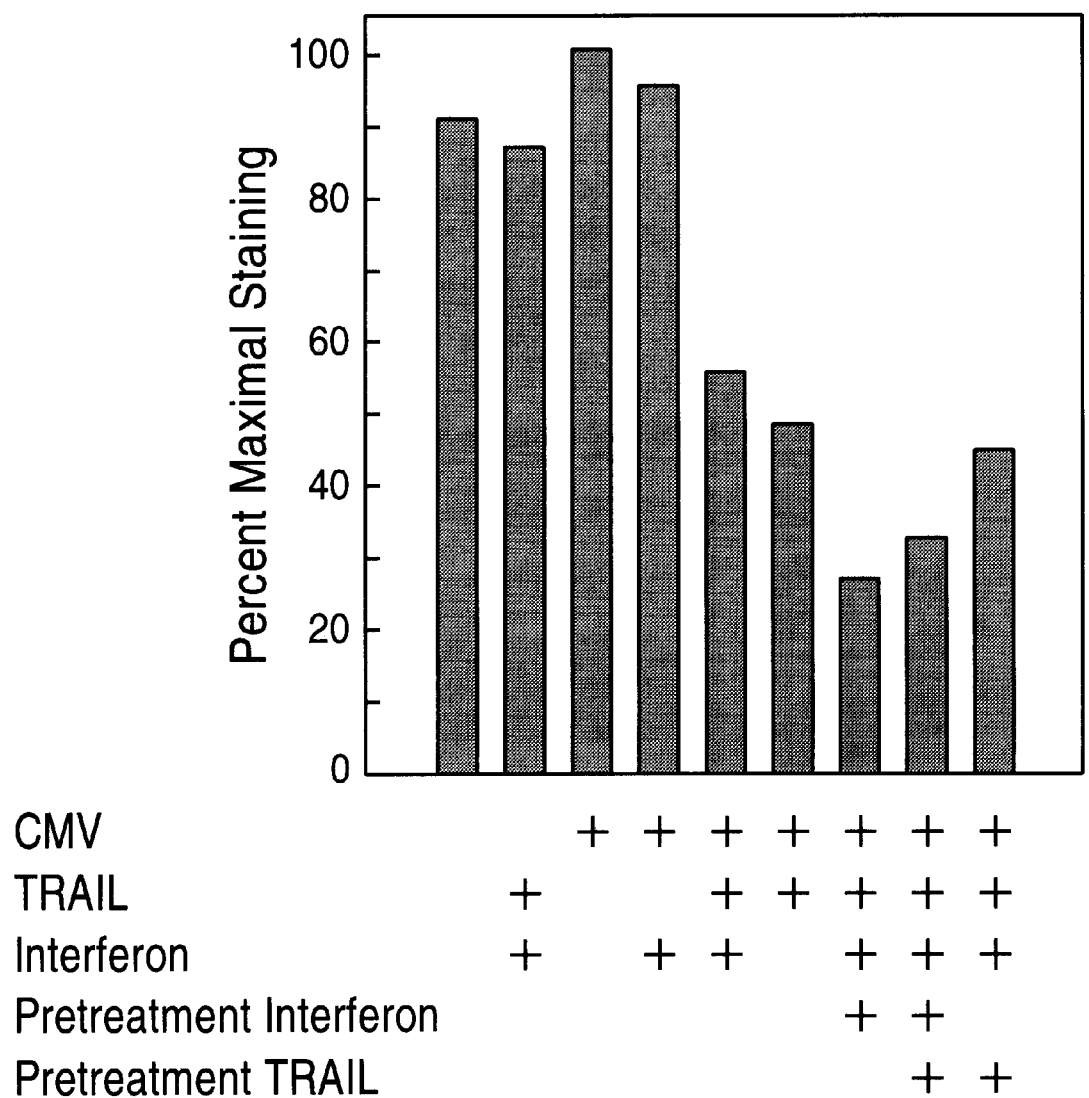
FIG. 2 presents the results of an assay described in example 11. Contact with a soluble human TRAIL polypeptide induced death of cytomegalovirus-infected human fibroblasts, whereas non-virally infected fibroblasts were not killed.

Normal human gingival fibroblasts were grown to confluency on 24 well plates in 10% $CO_2$ and DMEM medium supplemented with 10% fetal bovine serum, 100 µg/ml streptomycin, and 100 µg/ml penicillin. Samples of the fibroblasts were treated as indicated in FIG. 2. Concentrations of cytokines were 10 ng/ml for γ-interferon and 30 ng/ml of soluble Flag®-human TRAIL. All samples receiving TRAIL also received a two-fold excess by weight of anti-Flag® antibody M2 (described above), which enhances TRAIL activity (presumably by crosslinking).

Pretreatment of cells with the indicated cytokines was for 20 hours. To infect cells with cytomegalovirus (CMV), culture media were aspirated and the cells were infected with CMV in DMEM with an approximate MOI (multiplicity of infection) of 5. After two hours the virus containing media was replaced with DMEM and cytokines added as indicated. After 24 hours the cells were stained with crystal violet dye as described (Flick and Gifford, 1984, supra). Stained cells were washed twice with water, disrupted in 200 µl of 2% sodium deoxycholate, diluted 5 fold in water, and the OD taken at 570 nm. Percent maximal staining was calculated by normalizing ODs to the sample that showed the greatest staining. Similar results were obtained from several independent experiments.

The results presented in FIG. 2 demonstrate that TRAIL specifically killed CMV infected fibroblasts. This cell death was enhanced by pretreatment of the cells with γ-interferon. No significant death of non-virally infected fibroblasts resulted from contact with TRAIL.

EXAMPLE 12
Assay to Identify Blocking Antibodies

Blocking antibodies directed against TRAIL may be identified by testing antibodies for the ability to inhibit a particular biological activity of TRAIL. In the following assay, a monoclonal antibody was tested for the ability to inhibit TRAIL-mediated apoptosis of Jurkat cells. The Jurkat cell line is described in example 5.

A hybridoma cell line producing a monoclonal antibody raised against a Flag®/soluble human TRAIL fusion protein was employed in the assay. Supernatants from the hybridoma cultures were incubated with 20 ng/ml Flag®/soluble human TRAIL crosslinked with 40 ng/ml anti-Flag® monoclonal antibody M2, in RPMI complete media in a 96 well microtiter plate. An equivalent amount of fresh hybridoma culture medium was added to control cultures. The Flag®/soluble human TRAIL fusion protein and the monoclonal antibody designated M2 are described in example 7.

The hybridoma supernatant was employed at a 1:50 (v/v) dilution (starting concentration), and at two fold serial dilutions thereof. After incubation at 37° C., 10% $CO_2$, for 30 minutes, 50,000 Jurkat cells were added per well, and incubation was continued for 20 hours.

Cell viability was then assessed measuring metabolic conversion of alamar blue dye. An alamar blue conversion assay procedure is described in example 8. The monoclonal antibody was found to inhibit the apoptosis of Jurkat cells induced by Flag®/soluble human TRAIL.

EXAMPLE 13
TRAIL Blocking Study

Human microvascular endothelial cells of dermal origin were treated for 16–18 hours with plasma from patients with thrombotic thrombocytopenic purpura (TTP) or with control plasma, either alone or in the presence of anti-TRAIL polyclonal antiserum. A 1:2000 dilution of the antiserum was employed. The plasma was from two TTP patients, designated #1 and #2 below, The cells employed in the assays were MVEC-1 (HMVEC 2753, purchased from Clonetics, San Diego, Calif.) and MVEC-2 (DHMVEC 30282, purchased from Cell Systems, Kirkland, Wash.). Cultures of these cells can be maintained as described in Laurence et al. (*Blood,* 87:3245, 1996).

The results were as follows. The data shown are from DNA histograms of cells stained with propidium iodide, and "$A_0$ peak" represents the apoptotic peak (see Oyaizu et al., *Blood,* 82:3392, 1993; Nicoletti et al., *J. Immunol. Methods,* 139:271, 1991; and Laurence et al., *Blood,* 75:696, 1990).

| Microvascular EC | Plasma (1%) | Antibody | % $A_0$ peak |
|---|---|---|---|
| Experiment 1 | | | |
| Dermal MVEC-1 | control | — | 0 |
| Dermal MVEC-1 | TTP (#1) | — | 19.5 |
| Dermal MVEC-1 | TTP (#1) | + | 0.3 |
| Experiment 2 | | | |
| Dermal MVEC-2 | control | — | 0 |
| Dermal MVEC-2 | TTP (#2) | — | 20.0 |
| Dermal MVEC-2 | TTP (#2) | control Ab | 13.1 |
| Dermal MVEC-2 | TTP (#2) | + | 0.2 |
| Experiment 3 | | | |
| Dermal MVEC-1 | TTP (#1) | — | 50.1 |
| Dermal MVEC-1 | TTP (#1) | + | 10.6 |
| Experiment 4 | | | |
| Dermal MVEC-2 | control | — | 0 |
| Dermal MVEC-2 | TTP (#1) | — | 13.9 |
| Dermal MVEC-2 | TTP (#1) | control Ab | 14.1 |
| Dermal MVEC-2 | TTP (#1) | + | 0.6 |

The data reveal that plasma derived from TTP patients induces apoptosis of microvascular endothelial cells of dermal origin. This apoptosis was inhibited by polyclonal antibodies directed against TRAIL.

EXAMPLE 14
Expression of LZ-TRAIL

Examples of fusion proteins comprising leucine zipper (LZ) peptides fused to the N-terminus of a soluble TRAIL polypeptide are as follows. The leucine zipper moieties promote oligomerization of the TRAIL polypeptides fused thereto, as described above.

An expression vector is constructed, containing DNA encoding (from N- to C-terminus) a human growth hormone signal peptide, a leucine zipper peptide, and a soluble human TRAIL polypeptide. The TRAIL polypeptide comprises amino acids 95 to 281 of SEQ ID NO:2. This TRAIL polypeptide is a fragment of the extracellular domain of human TRAL, lacking the spacer region, as described in example 7.

The growth hormone signal peptide comprises the amino acid sequence: Met Ala Thr Gly Ser Arg Thr Ser Leu Leu Leu Ala Phe Gly Leu Leu Cys Leu Pro Trp Leu Gln Glu Gly Ser Ala (SEQ ID NO:19). The leucine zipper peptide is selected from peptides comprising the amino acid sequence:

$(Asp)_n$ $(Arg)_n$ Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, wherein each n independently represents 1 or 0 (SEQ ID NO:15);

Ser Leu Ala Ser Leu Arg Gln Gln Leu Glu Ala Leu Gln Gly Gln Leu Gln His Leu Gln Ala Ala Leu Ser Gln Leu Gly Glu (SEQ ID NO:16); or

Ser Ile Ala Ser Ile Arg Gln Gln Ile Glu Ala Ile Gln Gly Gln Ile Gln His Ile Gln Ala Ala Ile Ser Gln Ile Gly Glu (SEQ ID NO:17).

The fusion protein may comprise additional amino acid residue(s), encoded by DNA segments that result from construction of the vector, or that are added to facilitate vector construction. In one particular embodiment, the tripeptide Thr-Ser-Ser is positioned between the growth hormone signal peptide and the leucine zipper peptide. This tripeptide is encoded by a DNA segment that comprises an Spe I restriction endonuclease recognition site. The tripeptide Thr-Arg-Ser, encoded by a DNA segment that comprises a Bgl II restriction site, may be positioned between the leucine zipper and the TRAIL polypeptide.

DNA encoding the desired fusion protein is inserted into a suitable expression vector, such as the pDC409 vector described in example 7. CV1-EBNA cells are transformed with the recombinant expression vector, then cultured to allow expression of the fusion protein, and oligomerization thereof.

What is claimed is:

1. An antibody that specifically binds the human tumor necrosis factor related apoptosis inducing ligand (TRAIL) protein of SEQ ID NO:2.

2. An antibody according to claim 1, wherein said antibody is a monoclonal antibody.

3. An antibody of claim 1, wherein the antibody inhibits TRAIL-mediated apoptosis of a target cell.

4. An antibody of claim 1, wherein the antibody blocks binding of TRAIL to a target cell.

5. An antibody of claim 4, wherein said antibody is a monoclonal antibody.

6. An antigen-binding fragment of an antibody of claim 1.

7. An antigen-binding fragment of a monoclonal antibody of claim 5.

8. A hybridoma cell line that produces a monoclonal antibody of claim 2.

9. A composition comprising an antibody of claim 1, and a physiologically acceptable carrier, diluent, or excipient.

10. A composition comprising a monoclonal antibody of claim 2, and a physiologically acceptable carrier, diluent, or excipient.

11. An antibody of claim 3, wherein said antibody is an monoclonal antibody.

12. An antigen-binding fragment of a monoclonal antibody of claim 11.

13. An antibody that specifically binds a soluble human TRAIL polypeptide, wherein said polypeptide comprises amino acids x to 281 of SEQ ID NO:2, wherein x represents an integer from 39 to 95.

14. An antibody of claim 13, wherein said antibody is a monoclonal antibody.

15. An antibody of claim 13, wherein the antibody inhibits TRAIL-mediated apoptosis of a target cell.

16. A monoclonal antibody of claim 14, wherein the antibody blocks binding of TRAIL to a target cell.

17. An antigen-binding fragment of a monoclonal antibody of claim 14.

18. A hybridoma cell line that produces a monoclonal antibody of claim 14.

19. An antibody of claim 15, wherein said antibody is a monoclonal antibody.

20. An antibody that binds a polypeptide comprising amino acids 124 to 276 of SEQ ID NO:2.

21. An antibody of claim 20, wherein said antibody is a monoclonal antibody.

22. An antibody of claim 20, wherein the antibody inhibits TRAIL-mediated apoptosis of a target cell.

23. A monoclonal antibody of claim 21, wherein the antibody blocks binding of TRAIL to a target cell.

24. An antigen-binding fragment of a monoclonal antibody of claim 21.

25. An antibody of claim 22, wherein said antibody is a monoclonal antibody.

26. An antibody that binds a fragment of the TRAIL protein of SEQ ID NO:2, wherein the N-terminal amino acid of said fragment is selected from residues 39 to 124 of SEQ ID NO:2, and the C-terminal amino acid of said fragment is selected from residues 276 to 281 of SEQ ID NO:2.

27. An antibody of claim 26, wherein said antibody is a monoclonal antibody.

28. An antibody of claim 26, wherein the antibody inhibits TRAIL-mediated apoptosis of a target cell.

29. A monoclonal antibody of claim 27 wherein the antibody blocks binding of TRAIL to a target cell.

30. An antigen-binding fragment of a monoclonal antibody of claim 27.

31. A hybridoma cell line that produces a monoclonal antibody of claim 27.

32. A hybridoma cell line that produces a monoclonal antibody of claim 29.

33. An antibody of claim 28, wherein said antibody is a monoclonal antibody.

34. An antigen-binding fragment of a monoclonal antibody of claim 33.

35. A hybridoma cell line that produces a monoclonal antibody of claim 33.

* * * * *